US010532004B2

(12) United States Patent
Freeman et al.

(10) Patent No.: US 10,532,004 B2
(45) Date of Patent: Jan. 14, 2020

(54) SYNCHRONIZATION OF REPETITIVE THERAPEUTIC INTERVENTIONS

(71) Applicant: ZOLL Medical Corporation, Chelmsford, MA (US)

(72) Inventors: Gary A. Freeman, Waltham, MA (US); Daniel M. Lisogurski, Boulder, CO (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 22 days.

(21) Appl. No.: 14/926,259

(22) Filed: Oct. 29, 2015

(65) Prior Publication Data

US 2016/0199252 A1 Jul. 14, 2016

Related U.S. Application Data

(60) Continuation of application No. 12/779,111, filed on May 13, 2010, which is a division of application No. (Continued)

(51) Int. Cl.
*A61H 31/00* (2006.01)
*A61N 1/362* (2006.01)
(Continued)

(52) U.S. Cl.
CPC ......... *A61H 31/005* (2013.01); *A61B 5/0402* (2013.01); *A61H 31/00* (2013.01);
(Continued)

(58) Field of Classification Search
CPC ..................................................... A61H 31/00
(Continued)

(56) References Cited

U.S. PATENT DOCUMENTS 3,513,850 A 5/1970 Weber
3,865,101 A 2/1975 Saper et al.
(Continued)

FOREIGN PATENT DOCUMENTS

CN 1058538 A 2/1992
CN 1146319 A 4/1997
(Continued)

OTHER PUBLICATIONS

American Red Cross—Adult CPR/AED Training—Workplace Programs, http://www.redcross.org/hss/cpraed.html, printed from Internet May 14, 1999.
(Continued)

*Primary Examiner* — Eddy Saint-Vil
*Assistant Examiner* — William D Ermlick
(74) *Attorney, Agent, or Firm* — Zoll Medical Corporation

(57) ABSTRACT

A medical device of the type used for assisting a user in manually delivering repetitive therapy to a patient (e.g., chest compressions or ventilations in cardiac resuscitation), the device comprising a feedback device configured to generate feedback cues to assist the user in timing the delivery of the repetitive therapy, at least one sensor or circuit element configured to detect actual delivery times, at which the user actually delivers the repetitive therapy, and a processor, memory, and associated circuitry configured to compare the actual delivery times to information representative of desired delivery times to determine cue times at which the feedback cues are generated by the feedback device.

9 Claims, 14 Drawing Sheets

Related U.S. Application Data

12/639,133, filed on Dec. 16, 2009, now Pat. No. 9,283,140, which is a division of application No. 11/227,968, filed on Sep. 14, 2005, now Pat. No. 7,650,181.

(51) Int. Cl.
*A61M 5/142* (2006.01)
*A61B 5/0402* (2006.01)
*A61N 1/39* (2006.01)
*A61N 7/00* (2006.01)
*G06F 19/00* (2018.01)

(52) U.S. Cl.
CPC ......... *A61H 31/006* (2013.01); *A61H 31/007* (2013.01); *A61M 5/142* (2013.01); *A61N 1/3625* (2013.01); *A61N 1/3628* (2013.01); *G06F 19/00* (2013.01); *A61H 2201/501* (2013.01); *A61H 2201/5007* (2013.01); *A61H 2201/5043* (2013.01); *A61H 2201/5048* (2013.01); *A61H 2201/5084* (2013.01); *A61H 2201/5097* (2013.01); *A61H 2230/04* (2013.01); *A61H 2230/205* (2013.01); *A61H 2230/207* (2013.01); *A61H 2230/25* (2013.01); *A61H 2230/42* (2013.01); *A61N 1/39* (2013.01); *A61N 7/00* (2013.01)

(58) Field of Classification Search
USPC ...................................................... 434/265
See application file for complete search history.

(56) References Cited

U.S. PATENT DOCUMENTS

| | | | |
|---|---|---|---|
| 4,019,501 | A | 4/1977 | Harris |
| 4,077,400 | A | 3/1978 | Harrigan |
| 4,088,138 | A | 5/1978 | Diack et al. |
| 4,095,590 | A | 6/1978 | Harrigan |
| 4,193,064 | A | 3/1980 | Snyder |
| 4,198,963 | A * | 4/1980 | Barkalow ............ A61H 31/006 128/207.15 |
| 4,198,964 | A | 4/1980 | Honneffer |
| RE30,372 | E | 8/1980 | Mirowski et al. |
| 4,273,114 | A | 6/1981 | Barkalow et al. |
| 4,326,507 | A | 4/1982 | Barkalow |
| 4,360,345 | A * | 11/1982 | Hon ..................... G09B 5/065 434/262 |
| 4,491,423 | A | 1/1985 | Cohen |
| 4,588,383 | A | 5/1986 | Parker et al. |
| 4,610,254 | A | 9/1986 | Morgan et al. |
| 4,619,265 | A | 10/1986 | Morgan et al. |
| 4,757,821 | A | 7/1988 | Snyder |
| 4,797,104 | A | 1/1989 | Laerdal et al. |
| 4,863,385 | A | 9/1989 | Pierce |
| 4,928,674 | A | 5/1990 | Halperin et al. |
| 4,932,879 | A | 6/1990 | Ingenito et al. |
| 4,994,015 | A | 2/1991 | Cadwell |
| 5,081,993 | A | 1/1992 | Kitney et al. |
| 5,193,537 | A | 3/1993 | Freeman |
| 5,241,302 | A | 8/1993 | Thong |
| 5,247,945 | A | 9/1993 | Heinze et al. |
| 5,285,792 | A | 2/1994 | Sjoquist et al. |
| 5,330,526 | A | 7/1994 | Fincke et al. |
| 5,342,404 | A | 8/1994 | Alt et al. |
| 5,348,008 | A | 9/1994 | Bornn et al. |
| RE34,800 | E | 11/1994 | Hutchins |
| 5,391,187 | A | 2/1995 | Freeman |
| 5,409,010 | A | 4/1995 | Beach et al. |
| 5,431,685 | A | 7/1995 | Alt |
| 5,454,779 | A | 10/1995 | Lurie et al. |
| 5,466,244 | A | 11/1995 | Morgan |
| 5,472,453 | A | 12/1995 | Alt et al. |
| 5,474,574 | A | 12/1995 | Payne et al. |
| 5,496,257 | A | 3/1996 | Kelly |
| 5,507,778 | A | 4/1996 | Freeman |
| 5,511,553 | A | 4/1996 | Segalowitz |
| 5,514,097 | A | 5/1996 | Dillon |
| 5,533,958 | A | 7/1996 | Wilk |
| 5,562,710 | A | 10/1996 | Olsen et al. |
| 5,591,213 | A | 1/1997 | Morgan |
| 5,611,815 | A | 3/1997 | Cole et al. |
| 5,617,853 | A | 4/1997 | Morgan |
| 5,619,265 | A | 4/1997 | Suzuki et al. |
| 5,645,522 | A | 7/1997 | Lurie et al. |
| 5,645,571 | A | 7/1997 | Olson et al. |
| 5,662,690 | A | 9/1997 | Cole et al. |
| 5,700,281 | A | 12/1997 | Brewer et al. |
| 5,735,879 | A | 4/1998 | Gliner et al. |
| 5,787,880 | A | 8/1998 | Swanson et al. |
| 5,792,190 | A | 8/1998 | Olson et al. |
| 5,853,292 | A | 12/1998 | Eggert et al. |
| 5,913,685 | A | 6/1999 | Hutchins |
| 5,993,398 | A | 11/1999 | Alperin |
| 6,021,349 | A | 2/2000 | Arand et al. |
| 6,074,213 | A | 6/2000 | Hon |
| 6,120,442 | A | 9/2000 | Hickey |
| 6,125,299 | A | 9/2000 | Groenke et al. |
| 6,141,586 | A | 10/2000 | Mower |
| 6,155,257 | A | 12/2000 | Lurie et al. |
| 6,178,357 | B1 | 1/2001 | Gliner et al. |
| 6,179,793 | B1 * | 1/2001 | Rothman ............. A61H 9/0078 600/17 |
| 6,185,458 | B1 | 2/2001 | Ochs et al. |
| 6,193,519 | B1 | 2/2001 | Eggert et al. |
| 6,213,960 | B1 * | 4/2001 | Sherman ............... A61H 31/00 601/41 |
| 6,220,866 | B1 | 4/2001 | Amend et al. |
| 6,224,562 | B1 | 5/2001 | Lurie et al. |
| 6,238,349 | B1 | 5/2001 | Hickey |
| 6,296,490 | B1 * | 10/2001 | Bowden ............... G09B 23/288 434/265 |
| 6,306,107 | B1 | 10/2001 | Myklebust et al. |
| 6,334,070 | B1 | 12/2001 | Nova et al. |
| 6,351,671 | B1 | 2/2002 | Myklebust et al. |
| 6,356,785 | B1 | 3/2002 | Snyder et al. |
| 6,371,765 | B1 | 4/2002 | Wall et al. |
| 6,390,996 | B1 | 5/2002 | Halperin et al. |
| 6,405,082 | B1 * | 6/2002 | Borgenicht ............. A61N 1/39 607/5 |
| 6,428,323 | B1 | 8/2002 | Pugh |
| 6,438,417 | B1 | 8/2002 | Rockwell et al. |
| 6,443,735 | B1 | 9/2002 | Eggert et al. |
| 6,503,087 | B1 | 1/2003 | Eggert et al. |
| 6,572,547 | B2 | 6/2003 | Miller et al. |
| 6,575,914 | B2 | 6/2003 | Rock et al. |
| 6,638,073 | B1 | 10/2003 | Kazimirov et al. |
| 6,719,700 | B1 | 4/2004 | Willis |
| 6,752,771 | B2 | 6/2004 | Rothman et al. |
| 6,758,676 | B2 | 7/2004 | Eggert et al. |
| 6,827,695 | B2 | 12/2004 | Palazzolo et al. |
| 6,872,080 | B2 | 3/2005 | Pastrick et al. |
| 6,961,612 | B2 | 11/2005 | Elghazzawi et al. |
| 6,969,259 | B2 | 11/2005 | Pastrick et al. |
| 7,010,344 | B2 | 3/2006 | Burnes et al. |
| 7,072,712 | B2 | 7/2006 | Kroll et al. |
| 7,118,542 | B2 | 10/2006 | Palazzolo et al. |
| 7,122,007 | B2 | 10/2006 | Querfurth |
| 7,164,945 | B2 | 1/2007 | Hamilton et al. |
| 7,190,999 | B2 | 3/2007 | Geheb et al. |
| 7,192,284 | B2 * | 3/2007 | Eggert .................. G09B 23/30 434/267 |
| 7,220,235 | B2 | 5/2007 | Geheb et al. |
| 7,310,553 | B2 | 12/2007 | Freeman |
| RE40,471 | E | 8/2008 | Groenke et al. |
| 7,454,244 | B2 | 11/2008 | Kassab et al. |
| 7,706,878 | B2 | 4/2010 | Freeman |
| 7,761,139 | B2 | 7/2010 | Tearney et al. |
| 7,822,470 | B2 | 10/2010 | Osypka et al. |
| 7,837,669 | B2 | 11/2010 | Dann et al. |
| 7,846,138 | B2 | 12/2010 | Dann et al. |
| 8,012,135 | B2 | 9/2011 | Dann et al. |

(56) References Cited

U.S. PATENT DOCUMENTS

| | | | |
|---|---|---|---|
| 8,858,445 B2* | 10/2014 | Freeman | A61H 31/00 600/454 |
| 2001/0011159 A1 | 8/2001 | Cantrell et al. | |
| 2001/0018562 A1 | 8/2001 | Sherman et al. | |
| 2002/0024888 A1 | 2/2002 | Schreiber | |
| 2002/0026131 A1* | 2/2002 | Halperin | A61H 9/0078 601/41 |
| 2002/0026229 A1 | 2/2002 | Weil et al. | |
| 2002/0055694 A1* | 5/2002 | Halperin | A61B 5/04017 601/41 |
| 2002/0133197 A1 | 9/2002 | Snyder et al. | |
| 2002/0165471 A1 | 11/2002 | Halperin et al. | |
| 2002/0193711 A1 | 12/2002 | Halperin et al. | |
| 2003/0014055 A1 | 1/2003 | Svadovskiy | |
| 2003/0032988 A1 | 2/2003 | Fincke | |
| 2003/0055460 A1 | 3/2003 | Owen et al. | |
| 2003/0083699 A1 | 5/2003 | Hamilton et al. | |
| 2003/0158593 A1 | 8/2003 | Heilman et al. | |
| 2003/0192547 A1 | 10/2003 | Lurie et al. | |
| 2004/0039313 A1 | 2/2004 | Sherman et al. | |
| 2004/0039419 A1 | 2/2004 | Stickney et al. | |
| 2004/0044374 A1 | 3/2004 | Weinberg et al. | |
| 2004/0049118 A1 | 3/2004 | Ideker et al. | |
| 2004/0049232 A1* | 3/2004 | Ideker | A61N 1/3962 607/4 |
| 2004/0058305 A1 | 3/2004 | Lurie et al. | |
| 2004/0116969 A1* | 6/2004 | Owen | A61B 5/02416 607/6 |
| 2004/0162510 A1 | 8/2004 | Jayne et al. | |
| 2004/0162585 A1 | 8/2004 | Elghazzawi et al. | |
| 2004/0162586 A1 | 8/2004 | Covey et al. | |
| 2004/0162587 A1* | 8/2004 | Hampton | A61H 31/005 607/5 |
| 2004/0186525 A1 | 9/2004 | Burnes et al. | |
| 2004/0210171 A1* | 10/2004 | Palazzolo | A61B 5/04012 601/41 |
| 2004/0214148 A1 | 10/2004 | Salvino et al. | |
| 2004/0215244 A1* | 10/2004 | Marcovecchio | A61N 1/39 607/5 |
| 2004/0230140 A1* | 11/2004 | Steen | A61H 31/008 601/41 |
| 2004/0267325 A1 | 12/2004 | Geheb et al. | |
| 2005/0119706 A1* | 6/2005 | Ideker | A61H 31/00 607/5 |
| 2005/0209503 A1 | 9/2005 | Elliott | |
| 2005/0256415 A1* | 11/2005 | Tan | A61B 5/0464 600/509 |
| 2005/0261742 A1 | 11/2005 | Nova et al. | |
| 2006/0009809 A1* | 1/2006 | Marcovecchio | A61N 1/39 607/5 |
| 2006/0036292 A1 | 2/2006 | Smith et al. | |
| 2006/0089574 A1* | 4/2006 | Paradis | A61H 31/005 601/41 |
| 2006/0116724 A1 | 6/2006 | Snyder | |
| 2006/0173500 A1 | 8/2006 | Walker et al. | |
| 2006/0173501 A1* | 8/2006 | Stickney | A61B 5/046 607/5 |
| 2006/0224053 A1 | 10/2006 | Black et al. | |
| 2006/0229680 A1* | 10/2006 | Chapman | A61N 1/39 607/5 |
| 2006/0257377 A1 | 11/2006 | Atala et al. | |
| 2007/0049976 A1* | 3/2007 | Ni | A61N 1/37 607/9 |
| 2007/0054254 A1 | 3/2007 | Cook et al. | |
| 2008/0176199 A1 | 7/2008 | Stickney et al. | |
| 2018/0261128 A1* | 9/2018 | Tan | A61N 1/3925 |

FOREIGN PATENT DOCUMENTS

| | | |
|---|---|---|
| CN | 1559345 A | 1/2005 |
| GB | 2314648 | 1/1998 |
| JP | 2004-222785 | 8/2004 |
| WO | 96/10984 | 4/1996 |
| WO | 98/30282 | 9/1998 |
| WO | 98/39061 | 9/1998 |
| WO | 99/24114 | 5/1999 |
| WO | 99/25306 | 5/1999 |
| WO | 99/63926 | 12/1999 |
| WO | 99/65560 | 12/1999 |
| WO | 01/08629 | 2/2001 |
| WO | 01/56652 | 8/2001 |
| WO | 01/58522 | 8/2001 |
| WO | 01/66182 | 9/2001 |
| WO | 02/15836 | 2/2002 |
| WO | 02/072197 | 9/2002 |
| WO | 03/009895 | 2/2003 |
| WO | 04/037154 | 5/2004 |
| WO | 04/056303 | 7/2004 |
| WO | 04/073493 | 9/2004 |
| WO | 04/078259 | 9/2004 |
| WO | 05/021089 | 3/2005 |

OTHER PUBLICATIONS

Aase et al., "Compression Depth Estimation for CPR Quality Assessment Using DSP on Accelerometer Signals," IEEE Transactions on Biomedical Engineering, vol. 49, No. 3, Mar. 2002.

Force Sensing Resistors—An Overview of the Technology, FSR Integration Guide & Evaluation Parts Catalog with Suggested Electrical Interfaces (no date).

Gruben et al., "System for Mechanical Measurements During Cardiopulmonary Resuscitation in Humans," IEEE Transactions on Biomedical Engineering, vol. 37, No. 2, Feb. 1990.

Heartstream—The Background Behind Our Technology, http://www.heartstream.com/techbk.htm, printed from Internet Jun. 25, 1999.

Flewelling, Nellcor Incorporated, Noninvasive Optical Monitoring, Chap. 88, pp. 1346-1353. CRC Press, Inc., 1995.

Abella et al., Circulation. 2005; 111:428-434.

Crit Care Med 2000 vol. 28, No. 11 (Suppl.).

Sato et al., Critical Care Medicine, vol. 25(5), May 1997, pp. 733-736.

Yu et al., Circulation, 2002, Adverse Outcomes of Interrupted Precordial Compression During Automated Defibrillation.

Eftestol et al., Circulation, 2002, Predicting Outcome of Defibrillation by Spectral Characterization and Nonparametric Classification of Ventricular Fibrillation in Patients With Out-of-Hospital Cardiac Arrest.

M.R. Pinsky, Journal of Applied Physiology, vol. 60(2), pp. 604-612, Feb. 1986.

\* cited by examiner

SYSTEM BLOCK DIAGRAM

CLOSED LOOP CONTROL SYSTEM

RELAY OPERATOR $\hat{\gamma}_{\alpha\beta}$

MINOR HYSTERESIS LOOP

VARIABLE PHASER FUNCTION

HYSTERESIS CONTROLLER

METHOD OF PARAMETER BASED CPR

AUDIO PROCESSING

ADVISORY WITH CPR

SYNCHRONIZATION OF REPETITIVE THERAPEUTIC INTERVENTIONS

CROSS-REFERENCE TO RELATED APPLICATIONS

This application is a continuation application of and claims priority to U.S. application Ser. No. 12/779,111, filed May 13, 2010, which application is a divisional application of and claims priority to U.S. application Ser. No. 12/639,133, filed on Dec. 16, 2009, which application is a divisional application of and claims priority to U.S. application Ser. No. 11/227,968, filed on Sep. 14, 2005, issued U.S. Pat. No. 7,650,181. These applications are hereby incorporated by reference.

TECHNICAL FIELD

This invention relates to the field of medical devices for assisting in delivery of repetitive therapy, such as assisting rescuers in performing cardio-pulmonary resuscitation (CPR).

BACKGROUND

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. The term basic life support (BLS) involves all the following elements: initial assessment; airway maintenance; expired air ventilation (rescue breathing); and chest compression. When all three [airway breathing, and circulation, including chest compressions] are combined, the term cardiopulmonary resuscitation (CPR) is used.

There are many different kinds of abnormal heart rhythms, some of which can be treated by defibrillation therapy ("shockable rhythms") and some which cannot (non-shockable rhythms"). For example, most ECG rhythms that produce significant cardiac output are considered non-shockable (examples include normal sinus rhythms, certain bradycardias, and sinus tachycardias). There are also several abnormal ECG rhythms that do not result in significant cardiac output but are still considered non-shockable, since defibrillation treatment is usually ineffective under these conditions. Examples of these non-shockable rhythms include asystole, electromechanical disassociation (EMD) and other pulseless electrical activity (PEA). Although a patient cannot remain alive with these non-viable, non-shockable rhythms, applying shocks will not help convert the rhythm. The primary examples of shockable rhythms, for which the caregiver should perform defibrillation, include ventricular fibrillation, ventricular tachycardia, and ventricular flutter.

After using a defibrillator to apply one or more shocks to a patient who has a shockable ECG rhythm, the patient may nevertheless remain unconscious, in a shockable or non-shockable, perfusing or non-perfusing rhythm. If a non-perfusing rhythm is present, the caregiver may then resort to performing CPR for a period of time in order to provide continuing blood flow and oxygen to the patient's heart, brain and other vital organs. If a shockable rhythm continues to exist or develops during the delivery of CPR, further defibrillation attempts may be undertaken following this period of cardiopulmonary resuscitation. As long as the patient remains unconscious and without effective circulation, the caregiver can alternate between use of the defibrillator (for analyzing the electrical rhythm and possibly applying a shock) and performing cardio-pulmonary resuscitation (CPR). CPR generally involves a repeating pattern of five or fifteen chest compressions followed by a pause during which two rescue breaths are given.

Defibrillation can be performed using an AED. The American Heart Association, European Resuscitation Council, and other similar agencies provide protocols for the treatment of victims of cardiac arrest that include the use of AEDs. These protocols define a sequence of steps to be followed in accessing the victim's condition and determining the appropriate treatments to be delivered during resuscitation. Caregivers who may be required to use an AED are trained to follow these protocols.

Most automatic external defibrillators are actually semi-automatic external defibrillators (SAEDs), which require the caregiver to press a start or analyze button, after which the defibrillator analyzes the patient's ECG rhythm and advises the caregiver to provide a shock to the patient if the electrical rhythm is shockable. The caregiver is then responsible for pressing a control button to deliver the shock. Following shock delivery, the SAED may reanalyze the patient's ECG rhythm, automatically or manually, and advise additional shocks or instruct the caregiver to check the patient for signs of circulation (indicating that the defibrillation treatment was successful or that the rhythm is non-shockable) and to begin CPR if circulation has not been restored by the defibrillation attempts. Fully automatic external defibrillators, on the other hand, do not wait for user intervention before applying defibrillation shocks. As used below, automatic external defibrillators (AED) include semi-automatic external defibrillators (SAED).

Both types of defibrillators typically provide an auditory "stand clear" warning before beginning ECG analysis and/or the application of each shock. The caregiver is then expected to stand clear of the patient (i.e. stop any physical contact with the patient) and may be required to press a button to deliver the shock. The controls for automatic external defibrillators are typically located on a resuscitation device housing.

AEDs are typically used by trained medical or paramedic caregivers, such as physicians, nurses, emergency medical technicians, fire department personnel, and police officers. The ready availability of on-site AEDs and caregivers trained to operate them is important because a patient's chances of survival from cardiac arrest decrease by approximately 10% for each minute of delay between occurrence of the arrest and the delivery of defibrillation therapy.

Trained lay caregivers are a new group of AED operators. For example, spouses of heart attack victims may become trained as lay caregivers. Lay caregivers rarely have opportunities to defibrillate or deliver CPR, and thus they can be easily intimidated by an AED during a medical emergency. Consequently, such lay providers may be reluctant to purchase or use AEDs when needed, or might tend to wait for an ambulance to arrive rather than use an available AED, out of concern that the lay provider might do something wrong.

Some trained medical providers, e.g., specialists such as obstetricians, dermatologists, and family care practitioners, also rarely have the opportunity to perform CPR and/or defibrillate, and thus may be uneasy about doing so. Concerns about competence are exacerbated if training is infrequent, leading the caregiver to worry that he or she may not be able to remember all of the recommended resuscitation protocol steps and/or their correct sequence.

Similarly, both medical and lay caregivers may be hesitant to provide CPR and rescue breathing, or may be unsure when these steps should be performed, particularly if their training is infrequent and they rarely have the opportunity to use it.

It is well known to those skilled in the art, and has been shown in a number of studies, that CPR is a complex task with both poor initial learning as well as poor skill retention, with trainees often losing 80% of their initial skills within 6-9 months. It has thus been the object of a variety of prior art to attempt to improve on this disadvantageous condition. Aids in the performance of chest compressions are described in U.S. Pat. Nos. 4,019,501, 4,077,400, 4,095,590, 5,496,257, 6,125,299, and 6,306,107, 6,390,996. U.S. Pat. Nos. 4,588,383, 5,662,690 5,913,685, and 4,863,385 describe CPR prompting systems AEDs have always included voice prompts as well as graphical instructions on flip charts or placards since the earliest commercial versions in 1974, to provide both correct timing and sequence for the complex series of actions required of the rescuer as well as placement of the defibrillation electrodes. U.S. patent application Ser. No. 09/952,834 and U.S. Pat. Nos. 6,334,070 and 6,356,785 describe defibrillators with an increased level of prompting including visual prompts either in the form of graphical instructions presented on a CRT or on printed labels with backlighting or emissive indicia such as light emitting diodes AEDs since the 1970s have used the impedance measured between the defibrillation electrodes to determine the state of the AED as well as appropriate messages to deliver to the rescuer (e.g., "Attach Electrodes" if the initial prompts on the unit have been delivered and the impedance remains greater than some specified threshold; or to determine if there is excessive patient motion as in U.S. Pat. No. 4,610,254). U.S. Pat. No. 5,700,281 describes a device which uses the impedance of the electrodes to determine the state of the AED for delivering such messages as "Attach Electrodes."

Enhanced prompting embodied in these patents provides some benefit to the rescuer in improved adherence to the complex protocol required of them to successfully revive a cardiac arrest patient, but it has been discovered in testing of the AEDs generally employing elements of these patents that rescuers are still only able to achieve a performance level of less than about 50%. The methods of the study were as follows: None of the subjects had prior experience or training with an AED in order to eliminate the potential for bias due to previous AED training. The test subjects were presented with a simulated use scenario more accurately resembling than in previous studies what a lay rescuer would encounter in a cardiac arrest rescue situation. Four fully-functional defibrillators were used: Physio-Control LifePak CR Plus, ZOLL AED Plus, the Philips/Laerdal HeartStart OnSite, and the Cardiac Science PowerHeart. The test subjects were led into a simulated office, and told that a person, simulated by a manikin, had just fallen to the floor, appeared to be completely unconscious and could well be dying. They were told to use the AED and any other object in the office and act as if it were a real emergency. Each person was evaluated based on the number of actions taken that comprise the Chain of Survival Sequence (8 steps: check response, seek help, open airway, check breathing, give breathes, check circulation, remove clothing, and attach AED electrodes). It was found that the Medtronic (Minnesota) Lifepak CR Plus group, which comprised 11 lay rescuers, averaged 3.5±1.4 steps completed; the Cardiac Science (California) PowerHeart group, which comprised 11 lay rescuers, averaged 3.4±1.9 steps; the Philips (Massachusetts) HeartStart group, which comprised 12 lay rescuers, averaged 3.8±1.3 steps; and the ZOLL (Massachusetts) AEDPlus group, which comprised 11 lay rescuers, averaged 5.0±1.3 steps completed. Even the ZOLL device that was shown to be statistically better than the other devices only achieved a 63% compliance rate. Further, less than 10% of the test subjects were able to sustain the recommended 100 compressions per minute for at least one minutes' duration.

It has recently been recognized that good CPR is essential to saving more victims of cardiac arrest (*Circulation*. 2005; 111:428-434). In the cited study, researchers found that in 36.9% of the total number of segments, compression rates were less than 80 compressions per minute (cpm), and 21.7% had rates of less than 70 cpm. The compression rate recommended by the American Heart Association in their guidelines is greater than 100 cpm. In the study, higher chest compression rates were significantly correlated with initial return of spontaneous circulation (mean chest compression rates for initial survivors and non-survivors, 90±17 and 79±18 cpm, respectively; P=0.0033). Further, this study was performed using well-trained rescuers, including nurses and physicians, indicating that the problem of poor compression rates is widespread.

AEDs with CPR feedback such as those of ZOLL and Philips mentioned above have some form of compression rate prompting. This takes the form of a beep or tone at the desired rate of 100 compressions per minute as recommended by the American Heart Association guidelines. The ZOLL AEDPlus has the added feature that it will begin the compression rate tones at the rate that the rescuer begins their compressions, and then gradually increases the compression tone rate up to the desired rate of 100 cpm. In some cases, this approach may be helpful, but because the compression tone rate is asynchronous with the rescuer's compressions, the tones may occur out of phase with the rescuer compression rate, and may actually act to confuse the rescuer and momentarily slow them down.

AEDs have also been solely focused on defibrillation, which, while it provides the best treatment for ventricular fibrillation and certain tachycardias, is of no therapeutic benefit for the 60% of the cardiac arrest patients presenting in pulseless electrical activity (PEA) or asystole. As AEDs are becoming more prevalent in the home, there are also a host of other health problems that occur such as first aid as well as incidents related to chronic conditions such as asthma, diabetes or cardiac-related conditions for which the AED is of no benefit.

After a defibrillation shock, the heart is in one of two states: either the shock was successful and the heart is in a stunned, ischemic condition with very little myocardial ATP energy reserves necessary for rhythmic pacemaker activity and effective cardiac output, or the shock was unsuccessful. Surprisingly to some, a defibrillation rarely, if ever, converts ventricular fibrillation into a normal sinus rhythm with effective hemodynamic output. Good CPR is required after a successful defibrillation shock in order for a patient to survive.

Although automated chest compression devices, such as that described by U.S. Pat. No. 6,752,771 have been synchronized with the cardiac cycle, rescuers providing manual CPR generally compresses the chest at a fixed rate with no synchronization to the cardiac cycle of a damaged heart such as occurs with pulseless electrical activity (PEA). PEA is a condition where the heart is functioning electrically, but does not have enough healthy muscle fibers to contract effectively. Patients typically have a very low ejection fraction where most of the blood in the heart remains in the ventricles during the contraction rather than being ejected in to the aorta and coronary arteries.

Many studies have reported that the discontinuation of chest compressions, such as is commonly done for ECG analysis, can significantly reduce the recovery rate of spontaneous circulation and 24-hour survival rate. These studies include "Adverse effects of interrupting precordial compression during cardiopulmonary resuscitation" by Sato et al. (Critical Care Medicine, Volume 25(5), May 1997, pp 733-736); "Adverse Outcomes of Interrupted Precordial Compression During Automated Defibrillation" by Yu et al. (Circulation, 2002); and" Predicting Outcome of Defibrillation by Spectral Characterization and Nonparametric Classification of Ventricular Fibrillation in Patients With Out-of-Hospital Cardiac Arrest" by Eftestøl et al. (Circulation, 2002).

In the context of automatic, mechanical compression systems, it has long been recognized that there are beneficial effects of synchronizing cardiac compression and ventilation cycles to the cardiac cycle. M. R. Pinsky, "Hemodynamic effects of cardiac cycle-specific increases in intrathoracic pressure", Journal of Applied Physiology (Volume 60(2), pages 604-612, February 1986). U.S. Pat. Nos. 4,273,114, 4,326,507, and 6,752,771 describe mechanical compression systems that synchronize the compression cycle to the cardiac cycle. U.S. Patent application 2004/0162587 describes a mechanical compression system that modifies the chest compression based on monitored blood perfusion.

In U.S. Pat. No. 4,491,423 a resuscitation assistive timer is described that provides an audible compression rate that is adjusted based on the patient's age.

SUMMARY

In general, in a first aspect, the invention features a medical device of the type used for assisting a user in manually delivering repetitive therapy to a patient (e.g., chest compressions or ventilations in cardiac resuscitation), the device comprising a feedback device configured to generate feedback cues to assist the user in timing the delivery of the repetitive therapy, at least one sensor or circuit element configured to detect actual delivery times, at which the user actually delivers the repetitive therapy, and a processor, memory, and associated circuitry configured to compare the actual delivery times to information representative of desired delivery times to determine cue times at which the feedback cues are generated by the feedback device.

In preferred implementations, one or more of the following features may be incorporated. The manually delivered repetitive therapy may comprise manually delivered chest compressions as part of cardiac resuscitation. The actual delivery times and desired delivery times may comprise actual delivery phases and desired delivery phases. Actual delivery times and desired delivery times may be compared by forming differences between actual and desired delivery times. The cue times may be gradually shifted in time over a plurality of therapy deliveries to gradually shift the actual delivery times. The feedback cues may be audible or visual. The repetitive therapy may further comprise ventilation as part of cardiac resuscitation. The feedback cues may have at least two phases distinguishable by the user, with a first phase corresponding to a first phase of the delivered therapy, and a second phase of the feedback cue corresponding to a second phase of the delivered therapy. The repetitive therapy may comprise chest compressions for cardiac resuscitation, and the first phase of the feedback cue may correspond to the upstroke of the rescuer's compression movement, and the second phase of feedback cue may correspond to the downstroke of the rescuer's compression movement. The feedback cues may comprise audible sounds, and the first and second phases may differ in one or both of frequency and amplitude. The feedback cues may comprise an upstroke cue for chest compression, and the upstroke cue may vary in frequency, with the frequency increasing as the rescuer's body rises during upstroke prior to delivery of compression. The feedback cues may further comprise a downstroke cue that varies in frequency, with the frequency varying with time during delivery of compression. The downstroke cue may be shorter in duration than the upstroke cue. The downstroke cue may grow in volume, with crescendo at approximately the bottom of the delivered compression. The processor may be configured to determine a latency between cue times and actual delivery times, and to use the latency and the desired delivery times in determining the cue times. The processor may be configured to maintain a similar temporal relationship between cue times and actual delivery times. The similar temporal relationship may have the cue times occur prior to the actual delivery times. The processor may be configured to use a tracking filter to predict actual delivery times based on the user's past performance in delivering the repetitive therapy. The tracking filter may comprise a Kalman filter. The processor may be configured to compensate for a hysteresis relationship between cue times and actual delivery times. The tracking filter may be configured to limit the influence of brief departures of actual delivery times from desired delivery times. A low pass filter may provide the limit on influence of brief departures of delivery times. The desired delivery times may be selected based on measured physiology of the patient. The measured physiology may comprise the ECG of the patient. The desired delivery times may be times other than the T wave in the ECG. The measured physiology may be PEA of the heart, and the desired delivery times may be selected to produce actual chest compression times phased relative to the PEA to improve hemodynamic output. The measured physiology may be low level mechanical activity of heart, and the desired delivery times may be selected to produce actual chest compression times phased relative to the low level mechanical activity to improve hemodynamic output. The measured physiology may comprise the rhythm state of the heart, and the processor may be further configured to vary cue times in accordance with at least some changes in rhythm state. The rhythm state may be taken into account in deciding whether to phase feedback cues relative to the patient's underlying circulatory activity. The measured physiology may comprise the times of particular physiological events and the cue times may be selected to produce a desired temporal relationship between the times of the physiological events and the actual delivery times. The physiological events may be mechanical contractions of the heart. The desired delivery times may be shortly following pacing stimuli delivered to the heart, so that chest compressions occur during periods of improved myocardial tone resulting from the pacing stimuli.

In a second aspect of the invention, the invention features a medical device of the type used for assisting a user in manually delivering repetitive therapy to a patient, the device comprising a feedback device configured to generate feedback cues to assist the user in timing the delivery of the repetitive therapy, wherein the repetitive therapy comprises psychomotor activity on the part of the user delivering the therapy, and a processor, memory, and associated circuitry configured to generate feedback cues with at least two phases, a first phase corresponding to a first phase of the psychomotor activity and a second phase corresponding to a second phase of the psychomotor activity.

In preferred implementations, one or more of the following features may be incorporated. The manual repetitive therapy may be chest compression in manual cardiac resuscitation, and the first phase of psychomotor activity may comprise the upstroke movement by the user, and the second phase of the psychomotor activity may comprise the downstroke movement by the user.

In a third implementation, the invention features a medical device for assisting a user in manually delivering chest compressions to a patient as part of cardiac resuscitation, the device comprising a feedback device configured to generate feedback cues to assist the user in timing the delivery of the chest compressions, a processor, memory, and associated circuitry configured to determine cue times at which the feedback cues are generated by the feedback device, wherein the feedback cues have at least two phases distinguishable by the user, with a first phase corresponding to an upstroke phase of the rescuer's movement, and a second phase of the feedback cue corresponding to a downstroke of the rescuer's compression movement.

In preferred implementations, one or more of the following features may be incorporated. The feedback cues may comprise audible sounds, and the first and second phases may differ in one or both of frequency and amplitude. The feedback cues may comprise an upstroke cue for chest compression, and the upstroke cue may vary in frequency, with the frequency increasing as the rescuer's body rises during upstroke prior to delivery of compression. The feedback cue may further comprise a downstroke cue that varies in frequency, with the frequency varying with time during delivery of compression. The downstroke cue may be shorter in duration than the upstroke cue. The downstroke cue may grow in volume, with crescendo at approximately the bottom of the delivered compression.

In a fourth aspect, the invention features a medical device for assisting a user in manually delivering chest compressions and ventilations to a patient as part of cardiac resuscitation, the device comprising a feedback device configured to generate feedback cues to assist the user in timing the delivery of the chest compressions and ventilations, a processor, memory, and associated circuitry configured to determine cue times at which the feedback cues are generated by the feedback device, wherein the feedback cues are auditory, and the feedback cue for chest compressions is a different sound from the feedback cue for ventilations.

In preferred implementations, one or more of the following features may be incorporated. The difference in sound between the compression and ventilation cues may be a difference in tone. The feedback cue tone for compressions may overlap the feedback cue tone for ventilations on at least some occasions. The ventilation feedback cue may be a gradually changing sound with a duration that overlaps a plurality of compression feedback cues, which are of substantially shorter duration.

In a fifth aspect, the invention features a cardiac resuscitation device of the type used for assisting a user in manually delivering repetitive chest compressions to a patient, the device comprising a feedback device configured to generate non-verbal feedback cues to provide the user with feedback to assist the user with respect to at least one compression parameter, at least one sensor or circuit element configured to determine the user's performance with respect to the compression parameter, and a processor, memory, and associated circuitry configured to compare the user's actual performance with respect to the compression parameter to a desired performance with respect to the compression parameter, and to determine non-verbal feedback cues to assist the user in achieving performance closer to the desired performance.

In preferred implementations, one or more of the following features may be incorporated. The compression parameters may be one or a combination of more than one of the following parameters: compression depth; compression velocity; duty cycle; velocity of chest release; intrathoracic pressure during compressions; pleural pressures during compressions; sternal position, velocity, or acceleration; chest wall or sternum strain or deformation. The processor may be configured with a physiological model that relates delivery of the repetitive chest compressions to the at least one compression parameter.

In a sixth aspect, the invention features a method of automatically delivering chest compressions in cardiac resuscitation, comprising engaging the patient with a device for automatically delivering chest compressions at compression delivery times, detecting the timing of electrical pacing stimuli being delivered to the patient, and selecting the compression delivery times to be synchronized with a selected phase of electrical pacing stimuli.

In preferred implementations, one or more of the following features may be incorporated. The device delivering compressions may be separate from device delivering electrical pacing. The device may detect the timing of electrical pacing stimuli from electrodes on the patient.

In a seventh aspect, the invention features a method of delivering a second repetitive therapy while repetitive chest compressions are being delivered, comprising detecting the timing of the repetitive chest compressions, and delivering the second repetitive therapy at times that are synchronized to a selected phase of the repetitive chest compressions.

In preferred implementations, one or more of the following features may be incorporated. The second repetitive therapy may comprise electromagnetic pacing stimuli. The pacing stimuli may be subthreshold and may be configured to improve tone of myocardium. The pacing stimuli may be above threshold and may be configured to produce cardiac contractions. The chest compressions may be delivered manually. The chest compressions may be delivered by an automatic device. The feedback cues may be non-verbal cues.

In an eighth aspect, the invention features a medical device for assisting a user in manually delivering repetitive therapy to a patient, the device comprising a visual display for generating a visual, non-verbal feedback graphic to provide the user with a graphical indication of how well the repetitive therapy is being delivered, at least one sensor for sensing at least one parameter relating to how well the therapy is being delivered, and a processor, memory, and associated circuitry configured to process at least one output from at least one sensor to control the appearance of the graphical indication on the visual display.

In preferred implementations, one or more of the following features may be incorporated. The repetitive therapy may comprise chest compressions as part of cardiac resuscitation. The repetitive therapy may comprise ventilation as part of cardiac resuscitation. The graphical indication may comprise at least a first graphical element that provides the user with feedback generally on a compression by compression basis as to approximately how well individual compressions are being delivered. The graphical indication may further comprise at least a second graphical element that provides the user with feedback on an estimate of the cumulative impact of past compressions on coronary perfusion pressure. The first graphical element may be the color or other graphical aspect of the boundary of a bar element, and the second graphical element may be the percentage area within the bar element that bears a color or other graphical aspect. There may be at least two sensors and at least two parameters, and the graphical indication may comprise a first graphical element comprising a first indicator that moves along a first axis to convey a value of a first parameter and a second graphical element comprising a second indicator that moves along a second axis orthogonal to the first axis to convey a value of a second parameter. There may be at least three parameters, and the graphical indication may further comprise a third graphical element positioned at the intersection of the first and second axes, the third graphical element may configured to convey a value of a third parameter.

In a ninth aspect, the invention features an ultrasonic sensor system for measuring blood flow, the sensor system comprising an ultrasonic probe positioned at the end of a catheter, the probe and catheter being configured to be inserted into or at the opening of the esophagus, wherein the probe is configured to deliver and measure ultrasonic sound energy posteriorly toward the spine at approximately the cervical vertebra C3-C6, measuring the reflected ultrasound energy from both the vertebrae and blood vessels; and a processor, memory, and associated circuitry configured to process the output of the probe to estimate blood flow in an artery or vein by ultrasonic Doppler flow measurement.

In preferred implementations, one or more of the following features may be incorporated. The system may be combined with a cardiac resuscitation device and the estimated blood flow determined from the sensor output may be used in determining the timing of feedback cues delivered to the user. The sensor may be configured to be inserted into the esophagus and to deliver ultrasonic energy toward the cervical vertebrae to estimate blood flow in the vertebral artery.

In a tenth aspect, the invention features an ultrasonic sensor system for measuring blood flow, the sensor system comprising an ultrasonic probe positioned at the end of a catheter, the probe and catheter being configured to be inserted into or at the opening of the esophagus, wherein the probe is conically shaped such that it seats against the base of the pharynx at the superior end of the esophagus in the area of the esophageal muscle and the wide end of the probe just above that in the lower pharynx, wherein the probe is configured to deliver and measure ultrasonic sound energy laterally, and wherein the sensor is configured to deliver ultrasonic energy in a beam directed at an upward angle to intersect the common carotid artery and internal jugular vein; and a processor, memory, and associated circuitry configured to process the output of the probe to estimate blood flow in an artery or vein by ultrasonic Doppler flow measurement.

In preferred implementations, the processor may be configured to process the output of the ultrasonic probe to estimate blood flow velocity for both the carotid artery and jugular vein. The processor may be configured to calculate a pulsatile index as the difference of the peak aortic velocity and minimum diastolic velocity divided by the average velocity over one cardiac cycle. The processor may be configured to calculate a resistance index as the difference between the peak aortic velocity and minimum diastolic velocity divided by the peak aortic velocity.

The invention has many advantages, including the following (some of which may only be present in some aspects and some implementations):

Because the heart is in the early stages of recovery after a defibrillation shock, often with rhythmic electrical activity but degraded mechanical output, cardiac recovery is enhanced by the invention, for chest compressions are synchronized with the normal, if low level, mechanical activity of the recovering heart. The invention may help provide effective CPR for patients in non-perfusing, fibrillatory rhythms as well as for patients in hemodynamically unstable or ineffective rhythms such as PEA.

The invention's ability to synchronize chest compression to the activity of a damaged heart may improve perfusion. Without the invention, chest compressions may occur during ventricular filling, and thus be less effective, as the volume of blood in the heart is small and little or no blood is ejected in to the aorta and coronary arteries. A compression during this time may increase intrathoracic and/or diastolic pressures and further slow ventricular filling.

The invention may improve effectiveness of CPR during PEA because the compressions can be timed to occur during specific phases of systole such as isovolumetric contraction.

Asystolic rhythms may convert spontaneously to PEA during the course of CPR, and asynchronous delivery of chest compressions during PEA, as is typically currently performed, is substantially suboptimal with regard to circulatory hemodynamics. In these early stages of recovery, such as during post-shock PEA, the heart is actually contracting to some degree and asynchronous compression phasing may inflict additional stress on the myocardium as well as lower ejection fractions. The invention provides detection of the change of the heart from one rhythm state to the next and may provide feedback to the rescuer that synchronizes (entrains) the phase of the rescuer's CPR activities such as ventilation and chest compressions to the underlying electrical and mechanical activity of the heart and lungs. This has the advantages both of reducing the need for interruptions of chest compressions as well as improving hemodynamics.

The invention may provide feedback to a rescuer on a compression by compression basis, thus monitoring the quality of CPR (e.g. depth of compressions) as well as looking at the specific effects of the compression on the patient's heart. CPR guidelines necessarily cover the general population, and individual parameters such as depth or rate of compressions may not be optimal for individual victims. Assessment of individual compressions may be beneficial to the rescuer both in providing more effective CPR as well as conserving energy by not compressing the chest with more force or speed than required.

The invention may adjust the timing of feedback cues to synchronize them with actual compressions so that a rescuer does not get confused and disoriented by cues occurring unexpectedly at what appear to be odd times. By measuring latency of a cue and the time of onset of compression, the cues may be timed so that a cue does not depart too much from the normal latency. For example, where rescuer is tiring, and the rate of compressions is falling, the cue timing may be adjusted a little to encourage the rescuer to increase the rate, but adjustments may be done in such a way that only small changes in relative phase of compression and cue occur. In prior art, where only the rate of feedback cues was addressed, the relative phase of the cue and the onset of compression could be all over the place, and cause disorientation.

Other features and advantages of the invention will be found in the detailed description, drawings, and claims.

DETAILED DESCRIPTION

There are a great many different implementations of the invention possible, too many to possibly describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
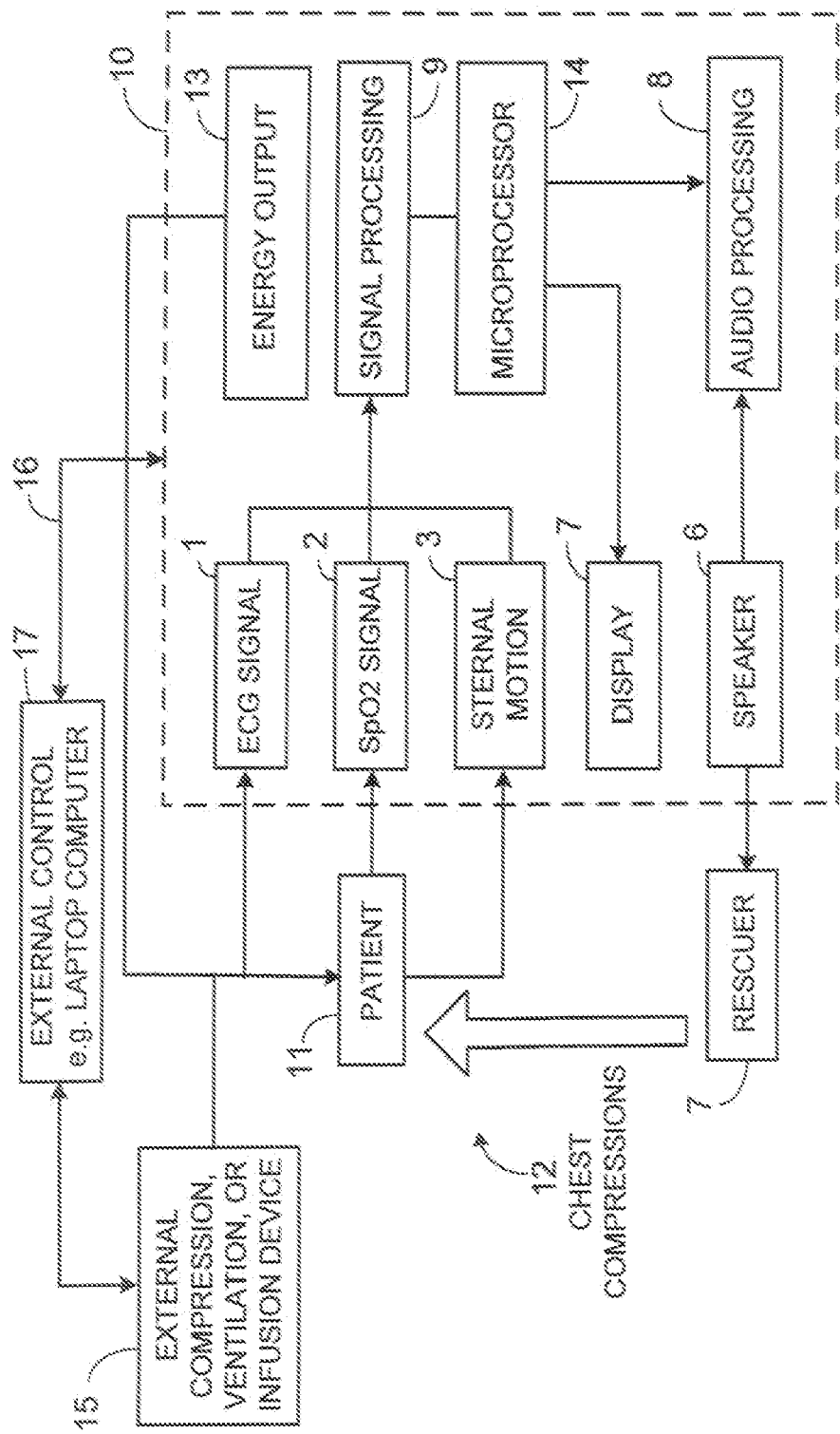
FIG. 1 is a system block diagram.

Referring to FIG. 1, one or more sensors or instruments 1, 2, 3 are used to acquire physiological signals from the patient. Pre-processing of certain signals may be required to derive relevant measurements or remove artifacts. For example, CPR artifact may be removed from the ECG signal using known techniques. In one such technique, sensor 3 detects when a compression actually occurs. This sensor could be an accelerometer located in a small plastic housing that resides underneath a rescuer's hands. Using signal processing methods (as disclosed in pending U.S. application Ser. No. 10/704,366, filed Nov. 6, 2003, entitled "Method and Apparatus for Enhancement of Chest Compressions During CPR," incorporated herein by reference), chest displacement is estimated by double integration of the acceleration signal. The time of onset of a chest compression 29 can be determined from the estimated displacement. The time of onset of a chest compression can be determined in other ways, including from transthoracic impedance, which is typically measured by AEDs, or from the artifact generated in the ECG by the chest compression. A speaker 6 generates a feedback tone 21 (one possible type of feedback cue), which we also refer to as the compression rate tone (CRT), at the desired rate and timing with regard to the cardiac cycle.

Figure 2:
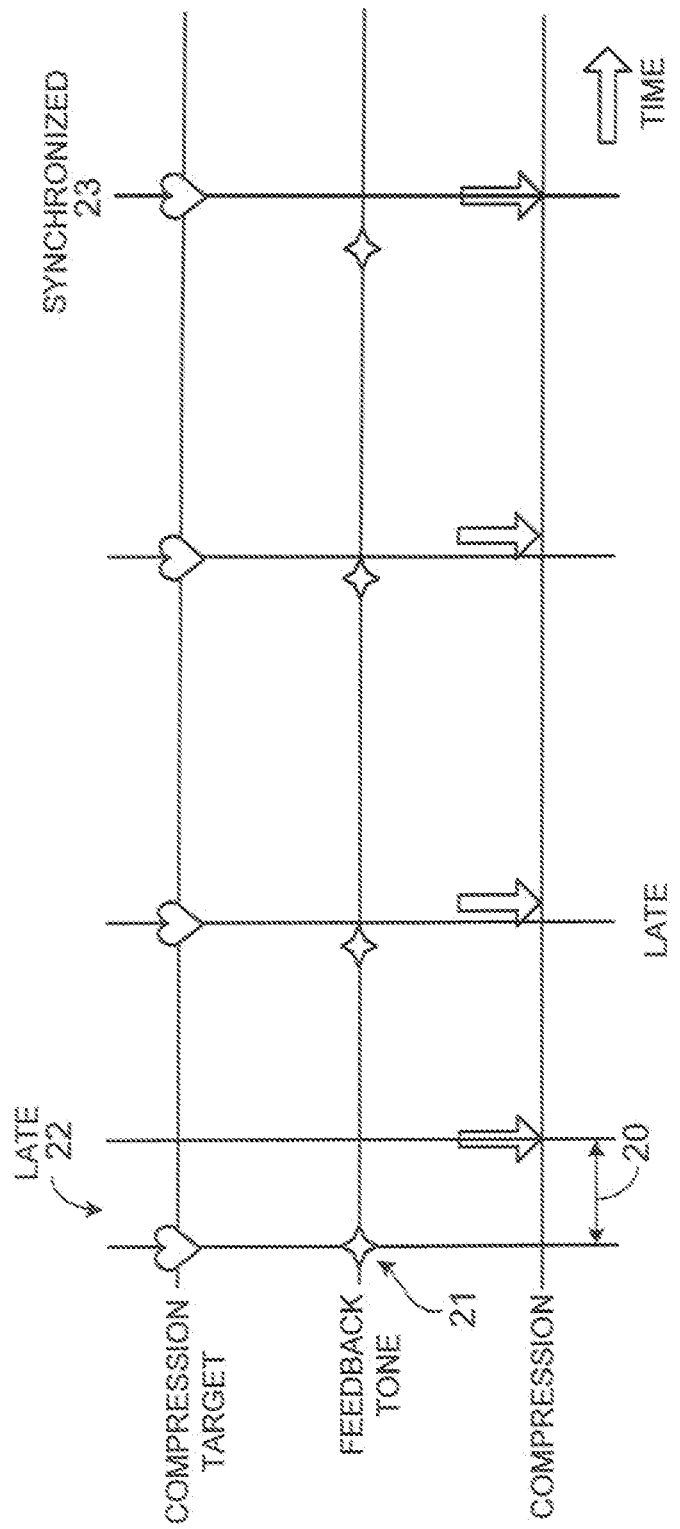
FIG. 2 is a depiction of examples of compression timing relative to feedback tone timing (changing from late to synchronized).

As shown in FIG. 2, the algorithm corrects for the rescuer's timing errors in performing chest compressions. In the example in FIG. 2, the algorithm measures the latency 20 between the calculated target compression time, the feedback tone 21, and the actual compression 29. The algorithm advances the feedback tone (CRT) to correct for the rescuer's latency 20 and detects when the compression is synchronized with the desired rate and phase of compressions (which has occurred by the fourth compression in the figure).

Although auditory tones are preferred for feedback cues to the rescuer, other forms of feedback cues could be provided to the rescuer, including visual signals.

The algorithm to convert input signals to feedback tones (or other compression feedback cues) may vary in complexity. The algorithm may be as simple as detecting a QRS complex or other point of interest in the ECG signal. Or it may involve more complex methods, including predictive tracking algorithms such as a Kalman filter or other methods using past readings to predict when the next compression should take place. The predicted time for a compression may be used to immediately update the time at which a feedback cue is delivered, or (as is shown in FIG. 2), the timing of the feedback cue may be adjusted slowly over multiple compressions, allowing a rescuer to slowly change the rhythm of compressions to bring compressions to the desired timing.

Figure 3:
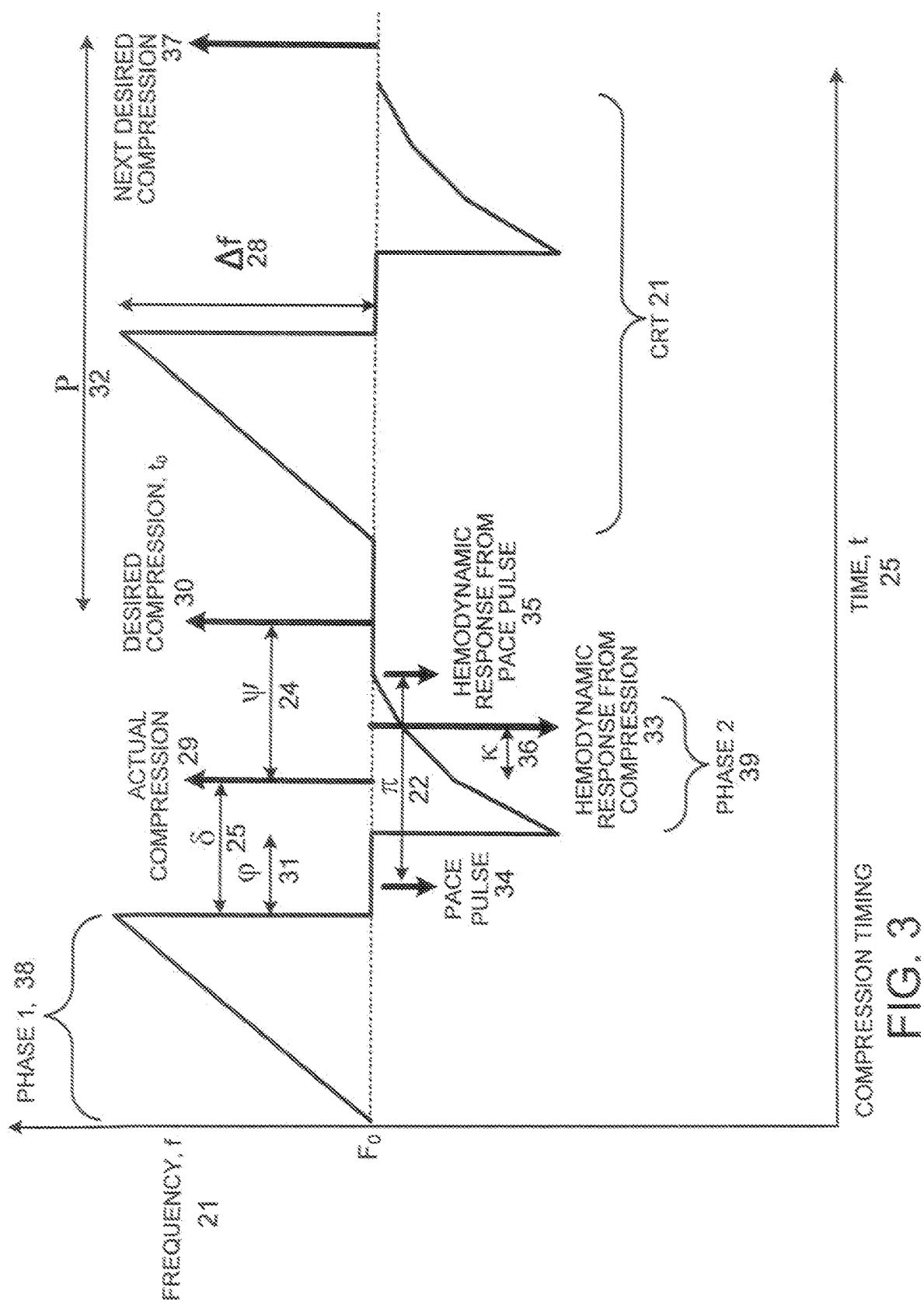
FIG. 3 is a detailed timing diagram showing the various parameters of feedback compression timing.

Referring to FIG. 3, in some implementations the feedback cue may have two phases (more than two phases are also possible). Using two phases addresses our discovery that the act of delivering chest compressions is primarily a biphasic psychomotor activity, with the rescuer's posterior muscle groups such as the erector spinalis and gluteus maximus involved in the preparatory upstroke phase of the compression cycle, and the anterior internal and external oblique muscle groups involved in the downstroke. A single-phase tone has the difficulty that it corresponds to the downstroke in the rescuer's mind, but significant preparatory activity is required before the downstroke can be delivered (i.e., the upstroke before the compression), and so the rescuer is required to anticipate when the next compression tone is going to occur so that his downstroke coincides with the single phase tone. This difficulty is believed to be the primary reason that compression tones as currently implemented in various CPR prompting devices are not as effective as they could be.

In some implementations, the frequency and volume of the feedback tone is varied between the phases (upstroke and downstroke). Frequency is used as an aural metaphor for the height of the rescuer's upper body from the victim, e.g., a tone that ramps up in frequency indicates the upstroke. In some implementations, the upstroke phase tone (UPT) 38 lasts for the amount of time that the rescuer performs the upstroke, making it possible for the rescuer to accurately follow the non-verbal instruction provided by the tone, and be properly positioned to begin the downstroke when the downstroke phase of the tone (DPT) 39 occurs. In some implementations, the DPT 39 is a shorter duration tone that ramps down in frequency fairly quickly, with the a crescendo in volume as the frequency decreases and with a maximum volume occurring at the point that would correspond to the bottom of the compression downstroke.

In other implementations, this approach can be applied to other multiphasic repetitive psychomotor activities, including ones with more than two phases, by providing a multiphasic tone whose phases are clearly delineated to the rescuer and for which the parameters of each phase of the tone are adjusted to assist synchronization of each phase of the psychomotor activity. Other possibilities for parameters of the feedback tone for each phase are bandwidth of a colored-noise signal or the volume envelope of a signal. For example, increasing the ramp rate of the envelope attack can be used to indicate to rescuers that they should increase the velocity of the downstroke of the compression.

Figure 4:
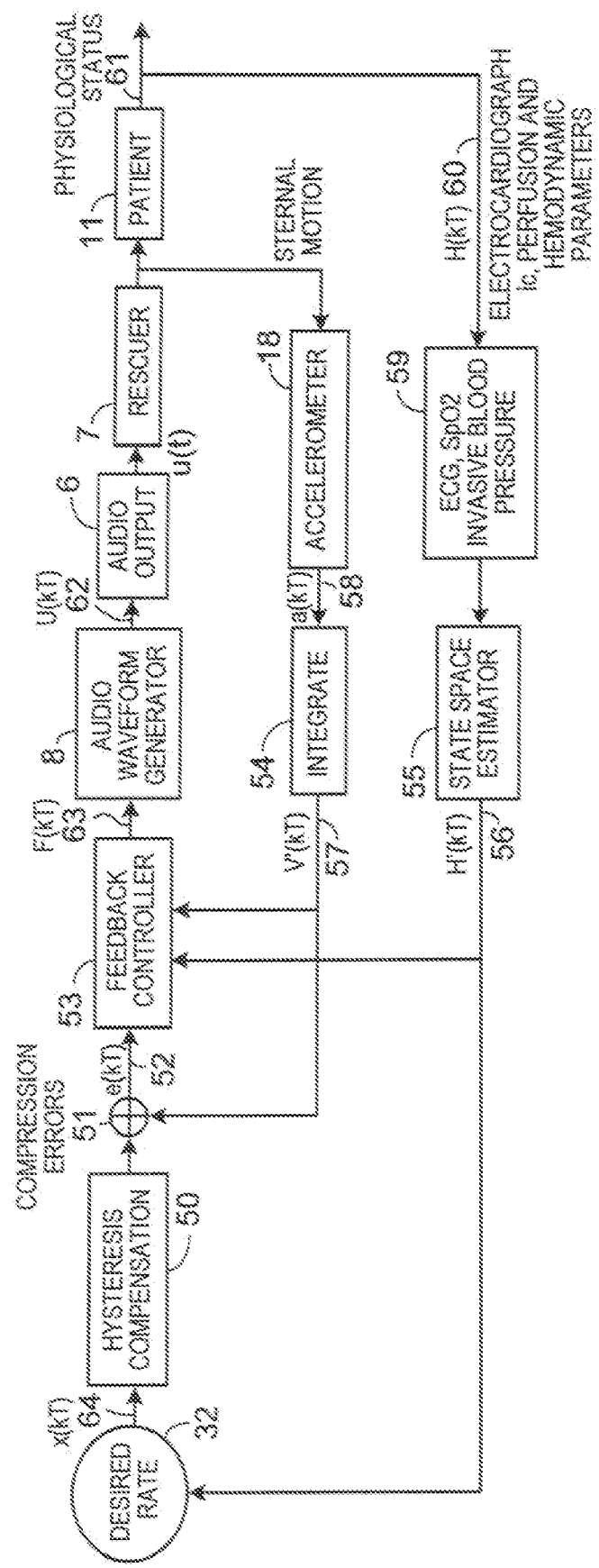
FIG. 4 is a block diagram showing a closed loop control system for phase synchronization (entrainment) of rhythmic resuscitation actions.

A block diagram for one possible control system for generating the feedback tones is shown in FIG. 4. A timing diagram is shown in FIG. 3. The control algorithm adjusts a feedback control vector F(kT+1) 63 (the vector includes UPT onset, φ, σ, $\Delta f^+$, $\Delta f^-$, $\varepsilon_{onset}$, $\varepsilon_{hold}$, $\varepsilon_{off}$) to minimize an error signal e(kT) 52, where T is the present sample interval. An input signal x(kT) 64 is the desired phase and rate for the compressions. X(kT) 64 may take the form of discrete times at which compressions are desired to occur, $t_0$, $t_0+1/f$, to + 2/f . . . , with corresponding times at which a compression was actually detected by the motion detection algorithm (which integrates 54 the output of an accelerometer sensor 18). X(kT) 64 may also take the form of a waveform vector describing the desired motion parameters of the rescuer's actions. The motion feedback signal preferably takes the form of a set of waveforms, vector V'(kT) 57, composed of the estimates of actual acceleration, velocity, and displacement waveforms. The error signal, e(kT) 52 is the difference of between V'(kT) 57 and the desired motion, x(kT) 64. Estimates, H'(kT) 56 are also made of the patient's physiological status, particularly the hemodynamic state as measured by such parameters as ECG 1, pulse oximetry 2, invasive blood pressure, and non-invasive blood pressure. H'(kT) 56 is fed back to adjust X(kT) 64 so that the rate and phase of X(kT) 64 are optimized to provide maximal benefit to the patient's current physiological state.

Referring also to FIGS. 3 and 4, there are several intervals that are calculated within the Feedback Controller Module (FCM) 53. Parameter δ (25) is the time difference between the end of UPT 38 and the time at which the compression actually occurred. Parameter ψ (24) is the time difference between the actual compression and the point in time the compression was desired to occur, $t_0$ (30). The desired compression time $t_0$ may correspond be a particular fiducial on an ECG 1 or pulse oximetry 2 waveform corresponding to the systolic phase of the cardiac cycle. Parameter φ (31) is the time difference between the end of UPT 38 and the onset of the DPT 39, and quantifies a natural anticipatory pause prior to the onset of DPT 39 and the action of compression downstroke by the rescuer. Parameter σ is the slope of frequency increase, measured in units of Hz/millisecond; (1/σ*Δf) is the length of time required for the UPT ramp, where Δf (28) is the total change in frequency during the UPT 38 phase.

The object of the closed loop control system of FIG. 4 is to reduce ψ, so that the actual compression occurs near the time of the desired compression time 30. If, however, the UPT 38 is too far out of phase with the rescuer's actual compressions, they will become confused and their performance will be adversely impacted. To provide a way or slowly adjusting the relative phase of the UPT and the rescuer's actual compressions, a moving factor, β, may be used, such that, $$\psi_{t+1}=\psi_t*\beta.$$

β may be a variable whose value is adjusted using conventional control system methods known to those skilled in the art such as proportional, difference, integral (PID), state space, or non-linear control methods. In the case where the underlying rhythm of the patient is asystole (no heart rhythm to synchronize the compressions to) and the system is only trying to cause the rescuer to deliver compressions at the correct rate, then to will not correspond to a physiological fiducial.

Feedback controller 53 (FIG. 4) will often have a low pass or median filter to minimize spurious error signals that may result, for example, from the rescuer's brief departures from delivery of well-timed compressions. The filter can be configured to switch its bandwidth depending on the state of the system. For instance, as is known in tracking systems, the filter's bandwidth may be initially set wide to acquire synchronization. But once the synchronization is acquired (the rescuer is regularly delivering compressions at an acceptable timing error relative to the desired compression times), the bandwidth may be switched to a more narrow setting to minimize the effects of short term timing errors by the rescuer. In other words, the state of the feedback system could change from "bad" compressions to "good" compressions based on the ratio ψ/P being less than 0.2 for more than three compressions (ψ/P is a normalized measure of how much error between the desired time for a compression and the actual compression is tolerable). The filter should also be configured to detect loss of synchronization—e.g., by looking for either a sudden or consistent increase in either the mean or standard deviation of ψ/P.

The governing equation of the process is constructed such that the compression period, P (32), is fixed and an estimation of the future interval, $\delta_{t+1}$, is calculated to determine when the next UPT onset should occur:

$$\text{UPT onset}=t_0+\{P-[\varphi-(\delta_{t+1}-\psi_{t+1})+(1/\sigma^*\Delta f)]\}$$

Tracking algorithms such as the Kalman filter may be used for the estimation and prediction of $(\delta_{t+1}-\psi_{t+1})$. The Kalman filter estimates a process by using a form of feedback control; the filter estimates the process state at some time and then obtains feedback in the form of (noisy) measurements. As such, the equations for the Kalman filter fall into two groups: time update equations and measurement update equations. The time update equations are responsible for projecting forward (in time) the current state and error covariance estimates to obtain the a priori estimates for the next time step. The measurement update equations are responsible for the feedback—i.e. for incorporating a new measurement into the a priori estimate to obtain an improved a posteriori estimate. The time update equations can also be thought of as predictor equations, while the measurement update equations can be thought of as corrector equations. Indeed the final estimation algorithm resembles that of a predictor-corrector algorithm for solving numerical problems.

Discrete Kalman filter time update equations:

$$\hat{x}_k^{\bar{k}}=A\hat{x}_{k-1}+Bu_{k-1}$$

$$P_k^{\bar{k}}=AP_{k-1}A^T+Q$$

Discrete Kalman filter measurement update equations:

$$K_k=P_k^{\bar{k}}H^T(HP_k^{\bar{k}}H^T+R)^{-1}$$

$$\hat{x}_k=\hat{x}_k^{\bar{k}}+K_k(z_k-H\hat{x}_k^{\bar{k}})$$

$$P_k=(I-K_kH)P_k^{\bar{k}}$$

The first task during the measurement update is to compute the Kalman gain, $K_k$. The next step is to actually measure the process to obtain, and then to generate an a posteriori state estimate by incorporating the measurement, $z_k$. The final step is to obtain an a posteriori error covariance estimate, $P_k$. After each time and measurement update pair, the process is repeated with the previous a posteriori estimates used to project or predict the new a priori estimates. This recursive nature is one of the very appealing features of the Kalman filter—it makes practical implementations much more feasible than (for example) an implementation of a Wiener filter which is designed to operate on all of the data directly for each estimate. The Kalman filter instead recursively conditions the current estimate on all of the past measurements. The equation, $$\hat{x}_k = \hat{x}_k^- + K_k(z_k - H\hat{x}_k^-)$$

is termed the predictor equation.

One of the primary limitations of the Kalman filter is that it only models a linear system with Gaussian distribution, not often encountered in the physiological setting. The best known algorithm to solve the problem of non-Gaussian, nonlinear filtering is the extended Kalman filter (EKF). This filter is based upon the principle of linearizing the measurements and evolution models using Taylor series expansions. The series approximations in the EKF algorithm can, however, lead to poor representations of the nonlinear functions and probability distributions of interest. As a result, this filter can diverge. Based on the hypothesis that it is easier to approximate a Gaussian distribution than it is to approximate arbitrary nonlinear functions other researchers have developed a filter termed the unscented Kalman filter (UKF). It has been shown that the UKF leads to more accurate results than the EKF and that in particular it generates much better estimates of the covariance of the states (the EKF often seems to underestimate this quantity). The UKF has, however, the limitation that it does not apply to general non-Gaussian distributions as is often the case with the ECG spectral distributions. Sequential Monte Carlo methods, also known as particle filters overcome this limitation and allow for a complete representation of the posterior distribution of the states, so that any statistical estimates, such as the mean, modes, kurtosis and variance, can be easily computed. Particle Filters can therefore, deal with any nonlinearities or distributions. Particle filters rely on importance sampling and, as a result, require the design of proposal distributions that can approximate the posterior distribution reasonably well. In general, it is hard to design such proposals. The most common strategy is to sample from the probabilistic model of the states evolution (transition prior). This strategy can, however, fail if the new measurements appear in the tail of the prior or if the likelihood is too peaked in comparison to the prior.

Some implementations use a estimator/predictor trajectory tracking technique known as the Unscented Particle Filter (UPF) as developed by Merwe, Doucet, Freitasz and Wan. Pseudocode for the UPF is as follows:

Unscented Particle Filter:
Initialization: t=0.
For i=1, ... N, draw states (particles) $x_0^{(i)}$ from the prior $p(x_0)$ and set, $$\bar{x}_0^{(i)} = E[x_0^{(i)}]$$

$$P_0^{(i)} = E[(x_0^{(i)} - \bar{x}_0^{(i)})(x_0^{(i)} - \bar{x}_0^{(i)})^T]$$

$$\bar{x}_0^{(i)a} = E[x^{(i)a}] = \begin{bmatrix} (\bar{x}_0^{(i)})^T & 0 & 0 \end{bmatrix}^T$$

$$P_0^{(i)a} = E[(x_0^{(i)a} - \bar{x}_0^{(i)a})(x_0^{(i)a} - \bar{x}_0^{(i)a})^T] = \begin{bmatrix} P_0^{(i)} & 0 & 0 \\ 0 & Q & 0 \\ 0 & 0 & R \end{bmatrix}$$

For t=1, 2, ... ,
a) Importance sampling step:
For i=1, ... N: Update particles with the UKF:
Calculate sigma points:

$$x_{i-1}^{(i)a} = [\bar{x}_{i-1}^{(i)a} \quad \bar{x}_{i-1}^{(i)a} \pm \sqrt{(n_a + \lambda)P_{i-1}^{(i)a}}]$$

Predict future particle (time update)

$$X_{i|t-1}^{(i)x} = f(X_{t-1}^{(i)x}, X_{t-1}^{(i)a})$$

$$\bar{x}_{t|t-1}^{(i)} = \sum_{j=0}^{2n_a} W_j^{(m)} X_{j,t|t-1}^{(i)x}$$

$$P_{t|t-1}^{(i)} = \sum_{j=0}^{2n_a} W_j^{(c)} [X_{j,t|t-1}^{(i)x} - \bar{x}_{t|t-1}^{(i)}][X_{j,t|t-1}^{(i)x} - \bar{x}_{t|t-1}^{(i)}]^T$$

$$Y_{i|t-1}^{(i)} = h(X_{t|t-1}^{(i)x}, X_{t-1}^{(i)a})$$

$$\bar{y}_{i|t-1}^{(i)} = \sum_{j=0}^{2n_a} W_j^{(m)} y_{j,t|t-1}^{(i)}$$

Incorporate new observation (measurement update)

$$P_{\bar{y}_t \bar{y}_t} = \sum_{j=0}^{2n_a} W_j^{(c)} [y_{j,t|t-1}^{(i)} - \bar{y}_{t|t-1}^{(i)}][y_{j,t|t-1}^{(i)} - \bar{y}_{t|t-1}^{(i)}]^T$$

$$P_{x_t y_t} = \sum_{j=0}^{2n_a} W_j^{(c)} [x_{j,t|t-1}^{(i)} - \bar{x}_{t|t-1}^{(i)}][y_{j,t|t-1}^{(i)} - \bar{y}_{t|t-1}^{(i)}]^T$$

$$K_t = P_{x_t y_t} P_{\bar{y}_t \bar{x}_t}^{-1}$$

$$\bar{x}_t^{(i)} = \bar{x}_{t|t-1}^{(i)} + K_t(y_t - \bar{y}_{t|t-1}^{(i)})$$

$$\hat{P}_t^{(i)} = P_{t|t-1}^{(i)} - K_t P_{\bar{y}_t \bar{y}_t} K_t^T$$

Sample $\hat{x}_t^{(i)} \sim q(x_t^{(i)} | x_{0:t-1}^{(i)}, y_{1:t}) = \mathcal{N}(\bar{x}_t^{(i)}, \hat{P}_t^{(i)})$ Set $\hat{x}_{0:t}^{(i)} \triangleq (x_{0:t-1}^{(i)}, \hat{x}_t^{(i)})$ and $\hat{P}_{0:t}^{(i)}(P_{0:t-1}^{(i)}, \hat{P}_t^{(i)})$ For i=1, ... N, evaluate the importance weights up to a normalizing constant:

$$w_t^{(i)} \propto \frac{p(y_t | \hat{x}_t^{(i)}) p(\hat{x}_t^{(i)} | x_{t-1}^{(i)})}{q(\hat{x}_t^{(i)} | x_{0:t-1}^{(i)}, y_{1:t})}$$

For i=1, ... N, normalize the importance weights.
b) Selection Step
Multiply/Suppress particles, $(\hat{x}_{0:1}^{(i)}, \hat{P}_{0:1}^{(i)})$ with high/low importance weights, $\tilde{w}_1^i$ respectively, to obtain N random particles.

c) Output: The output of the algorithm is a set of samples that can be used to approximate the posterior distribution as follows:

$$p(x_{0:t} | y_{1:t}) \approx \hat{p}(x_{0:t} | y_{1:t}) = \frac{1}{N} \sum_{i=1}^{N} \delta_{(x_{0:t}^{(i)})}(dx_{0:t})$$

Resulting in the estimate of, $$E(g_t(x_{0:t})) = \int g_t(x_{0:t}) p(x_{0:t} | y_{1:t}) dx_{0:t} \approx \frac{1}{N} \sum_{i=1}^{N} g_t(x_{0:t}^{(i)})$$

for some function of interest, $g_t$, for instance the marginal conditional mean or the marginal conditional covariance or other moment.

It has been shown in numerous studies on the psychology of perception as well as usability testing of user interfaces that users have a poor ability to quantify short durations of time, but are excellent at discerning temporal order, i.e., whether or not the compression feedback occurred before or after the actual compression. It is thus typically advantageous that the delay, δ (25), always be positive, since small absolute shifts of δ that cause it to oscillate about zero can result in larger adverse oscillations in the phase alignment of the rescuer compressions.

This inability of the rescuer to discern small changes in time duration means that there is, in effect, a dead band relationship between the desired and actual compression timing. Within this dead band, a change in the timing of a feedback cue may not produce a change in the user's perception of the desired timing. Such dead bands produce what is commonly referred to as hysteresis. Hysteresis—the influence of the previous history or treatment of a body on its subsequent response to a given force or changed condition—is widely found in nature. It was first recognized in ferromagnetic materials, and subsequently in plasticity, friction, and phase transitions, as well as in somewhat different fields such as mechanics, thermodynamics, biology, chemistry, and economics, among others. Hysteresis is present when the transfer function of the system changes depending on whether the input to the system is increasing or decreasing.

Figure 5:
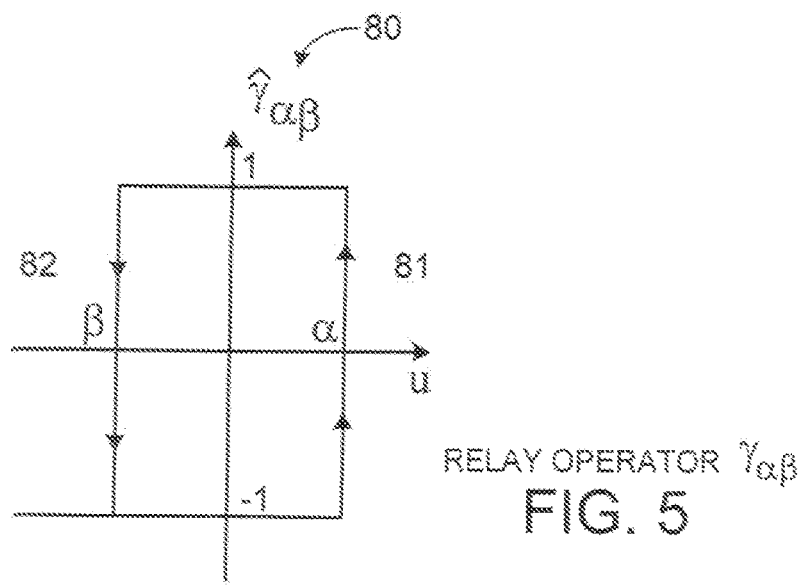
FIG. 5 is a plot showing an example of a hysteretic relay operator.
Figure 6A:
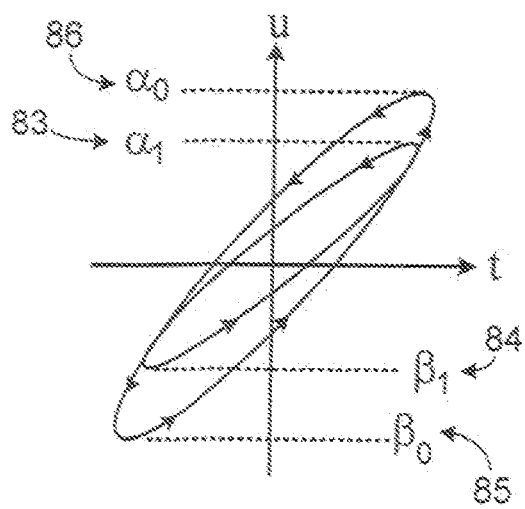
FIGS. 6A and 6B are plots showing examples of a minor hysteresis loop.
Figure 6B:
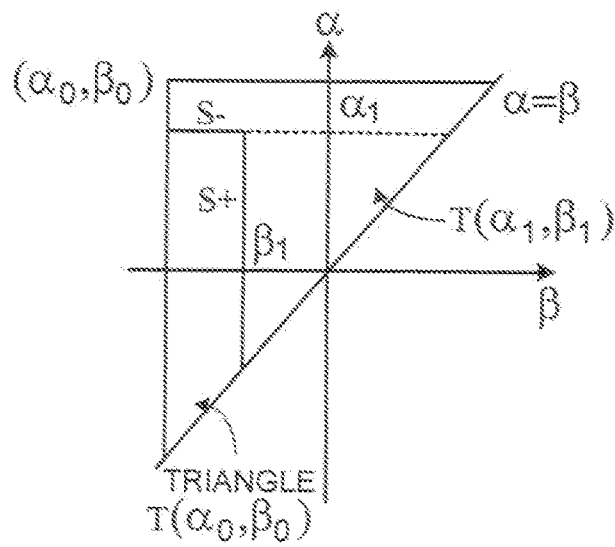

Referring to FIGS. 5, 6A and 6B, the Preisach Model is often used to represent hysteresis with non-local memory, i.e., the future values of the output y(t), for t>$t_0$, depend not only on y($t_0$), but also on past extrema of the input. The Preisach Model, in particular, considers an infinite set of relay operators $\gamma_{\alpha\beta}$ 80, where α 81 and β 82 correspond to the ascending and descending switching values where the output switches between −1 and +1.

In a restricted frequency range, it is possible to consider that hysteresis is rate independent and acts as an additive disturbance on the linear dynamics of the system. Here, a system with hysteresis is seen as a parallel connection of a linear dynamical system with a rate independent hysteresis with memory. In operator form the system can be represented by:

$$y = L[u] + \hat{\Gamma}[u]$$

where $\hat{\Gamma}$ represents the rate independent hysteresis with memory and L represents the dynamics of the system. The weighted response of an infinite collection of relays is summed over all possible switching values:

$$y(t) = \hat{\Gamma}[u(t)] = \iint_H \mu_{\alpha,\beta} \hat{\gamma}_{\alpha,\beta}[\mu(t)] d\alpha d\beta$$

FIGS. 6A and 6B show a minor hysteresis loop created after an input signal is varied between $\alpha_1$ 83 and $\beta_1$ 84. The triangle $T(\alpha_1, \beta_1)$ is added to the positive set $S^+$ and subtracted from the negative set $S^-$ when the input reaches $\alpha_1$, and subtracted from $S^+$ when the input reaches $\beta_1$ 84. When the input is at $\alpha_1$ 83 the interface line L(t) is just a line parallel to the β axis, creating a set of past extrema with one corner at the intersection $\alpha_1$ 83 and $\beta_0$ 85. When the input is at $\beta_1$ 84, triangle $T(\alpha_1, \beta_1)$ is added to the negative set $S^-$, and the interface line L(t) is a step as shown in FIGS. 6A and 6B. This difference is what causes the loop to trace two different curves.

Figure 7:
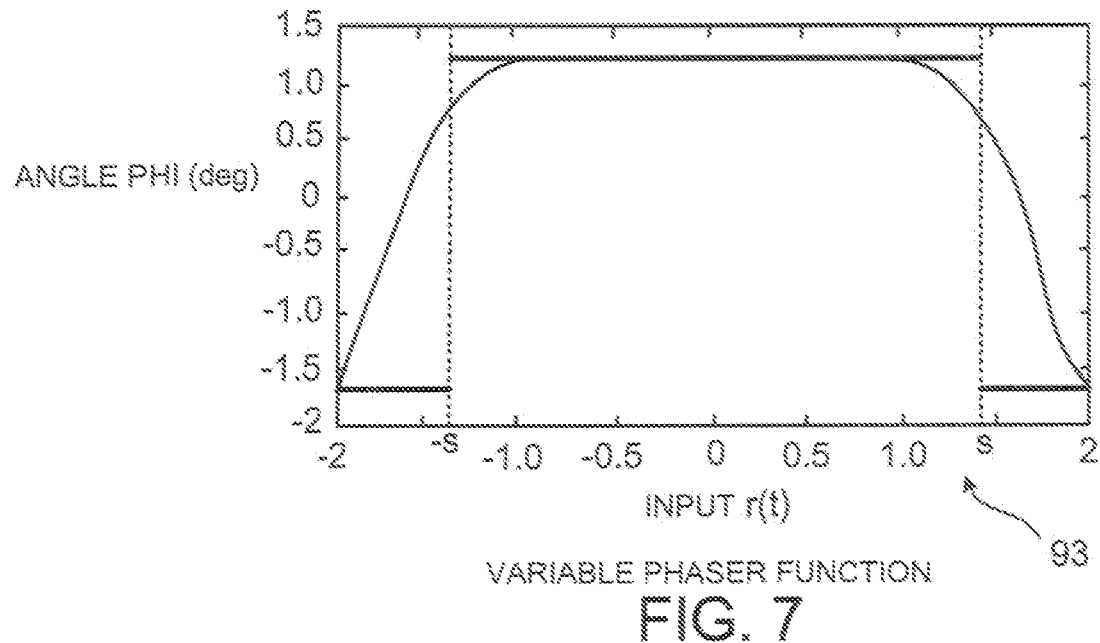
FIG. 7 is a plot showing a variable phaser function.
Figure 8:
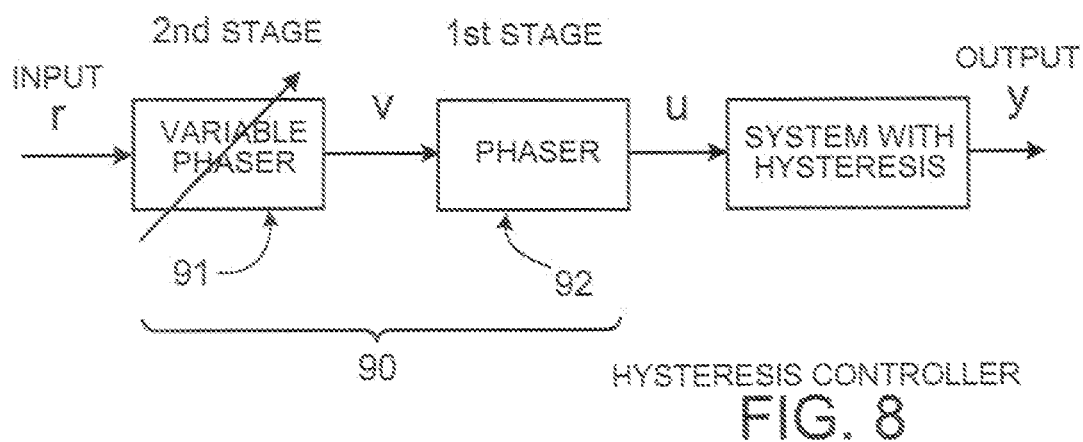
FIG. 8 is a block diagram showing a hysteresis controller.

Referring to FIGS. 5-8, the Hysteresis Controller 90 is two-staged: it uses the "phaser" operator 92 that shifts its periodic input signal by a constant phase angle for the first stage, and a variable phaser 91, shown in FIG. 7, for the second stage, governed by the equation:

$$v(t) = \begin{cases} \cos(\phi_1) r(t) + \frac{\sin(\phi_1)}{\omega} \dot{r}(t) & \text{if } |r| \leq s \\ \cos(\phi_2) r(t) + \frac{\sin(\phi_2)}{\omega} \dot{r}(t) & \text{if } |r| > s \end{cases}$$

where $\varphi_1 \geq 0$ and $\varphi_2 \leq 0$, and s 93 is empirically determined. An approximation of the discontinuous function depicted by the bold, solid lines in FIG. 7 is sometimes employed using the hyperbolic tangent function as shown by the light, solid line.

The feedback provided the rescuer 7 may be implemented in a variety of forms, including as visual and auditory cues (which are believed to be most effective).

Various types of information on the patient's physiology may be used as input to determine the timing of the feedback. For example, any of the following physiological signals, or combinations of physiological signals, could be used: ECG; measures of cardiac output; measures of heart rate; blood pressure(s); oxygen saturation ($SpO_2$); heart sounds (including phonocardiography); heart imaging (including ultrasound); impedance cardiography.

The feedback cues could address a variety of compression parameters other than compression timing, including, for example, any of the following, or combinations of the following: compression velocity; compression depth; duty cycle; velocity of chest release; intrathoracic pressures during compressions; pleural pressures during compressions; sternal position, velocity or acceleration; chest wall or sternal strain or deformation.

In some implementations, the quality of the chest compressions is monitored, and the feedback cues varied to improve quality. For instance the following compression parameters have been shown to have significant effect on the hemodynamic effects of chest compressions: the depth of the compression, the velocity of the compression downstroke (improving the ejection fraction and systolic effectiveness), and achievement of a rapid and complete release of pressure from the sternum during the upstroke of compression (thereby improving diastolic filling of the heart). By varying the feedback cues, it is possible to improve both the timing and quality of compressions. The proper compression depth is specified by AHA recommendations at 2 inches. It has been shown in animal and theoretical models that the velocity of compression and full release of pressure from the sternum may be equally important to depth of compression. In some implementations, the system may increase the frequency variation Δf (28) during the upstroke cue (UPT) 38, with the result that the rescuer will further release his hands from the patient's sternum during the decompression phase. In some implementations, increasing the audio volume of the downstroke cue (DPT) 39 and the amplitude envelope may cause a rescuer to increase the velocity of the compression downstroke. Also, the duty cycle of CPR compressions (i.e., the percentage of time devoted to upstroke versus downstroke) may be varied (e.g., in response to measured activity of the heart) by adjusting the relative ratio of time devoted to the UPT and DPT cues (e.g., lengthening the time devoted to the DPT cue may achieve a longer downstroke by the rescuer).

In other implementations, feedback may be provided to the rescuer for timing delivery of ventilation. This may be helpful in preventing over-ventilation as well as controlling intrathoracic pressures. Pressures from chest compressions and ventilations are an important factor in assisting venous return of blood to the heart as well as ejecting blood from the ventricles. The currently recommended ratio between compressions and ventilations is 15:2 for adults. Like the compression cycle, a ventilation cycle using a Bag Valve Mask (BVM) can be represented to the rescuer as a biphasic sequence composed of the phase of squeezing the bag and the phase of releasing the bag. The biphasic audio tone for ventilation is distinct from that used for compressions. This can be accomplished by making the respective feedback tones for compressions and ventilation recognizable and distinct, preferably from a perceptually classifiable perspective. For instance, the tone for compressions might have the waveshape and harmonics such that it is perceived as a trumpet while the ventilation might have the waveshape and harmonics such that it is perceived as a violin. Using techniques common to sound synthesis the fundamental frequency may be shifted for each of the tones to provide the change in frequency necessary for feedback.

In other implementations, wherein an automated chest compression device and/or automated ventilator is available during a rescue, the automated chest compressions and/or ventilation delivered by the automated device may be synchronized with the cardiac activity induced by repetitive cardiac stimulation therapy such a electrical pacing. Pacing can also be induced by magnetic stimulation (U.S. Pat. Nos. 4,994,015 and 5,078,674) or mechanically induced stimulation using ultrasonic transducers. The induced hemodynamic response of the heart will vary from patient to patient and it is desirable that the mechanical compression delivered by the automated chest compression device be synchronized to the induced hemodynamic response in order to maximize blood flow and reduce energy consumption of the myocardial tissue. The start time of the compression pulse, $t_c$, is also adjusted relative to the start time of the pacing, $t_p$, such that $t_p - t_c = \kappa - \pi$, where $\kappa$ (36) is the delay from the start of a compression to the hemodynamic response and $\pi$ (22) is the delay from the start of a pacing pulse to the hemodynamic response. As the patient condition changes during the course of a reuscitation, the values of $\pi$ and $\kappa$ will change as drugs such epinephrine and amiodarone are delivered which have effects on vascular tone and calcium and beta-channel-related excitation-contraction (EC) coupling dynamics. As with the embodiment for manual compressions, a predictive algorithm which is used for the control of a mechanical compression device or inflatable vest can be used to take into account the changes in the response of the patient, with the results of the predictive algorithm applied to timing of compressions applied by the device. Synchronization may be achieved either through direct communication between devices such as a serial Universal Serial Bus (USB) interface or wirelessly using a low-latency wireless protocol such as the so-called ZigBee, IEEE 802.15.4 protocol standard.

Pacing may also be combined, in some implementations, with manual compressions as a means of augmenting the rescuer's mechanical compressions with the electrically-induced contractions of the myocardium. In these implementations, $\pi$ may be adjusted relative to $\delta$ such that the hemodynamic response of the electrically-induced activity slightly preceeds that induced by the manual compression by the rescuer, on the order of 50-100 milliseconds. During a resuscitation, the heart is in a state of profound ischemia resulting in a flacidity and loss of tone as lactate builds up in the myocardium and the tissue pH drops. As a result of the loss of tone, the heart becomes a less-effective pump structure for generating blood flow during manual chest compressions. Drugs such as epinephrine act to improve tone, but because they are delivered venously, their action may take 2-3 minutes during cardiac arrest, when the only blood flow is that induced by the chest compressions. Pacing that may or may not be sufficient to actually cause a satisfactory hemodynamic response as a result of the metabolically compromised state of the myocardium can sufficiently improve the tone of the myocardium immediately prior to, and synchronized with, the mechanical compression without the therapeutic delay experienced with drugs such as epinephrine. This instantaneous improvement in myocardial tone can substantially improve the hemodynamic effectiveness of the mechanical compression.

In other implementations, feedback of the various parameters related to the therapeutic interventions such as compressions and ventilations are fed back to the rescuer based on both the state of the patient and the quality of the compressions. In some simpler implementations, the system provides feedback in such a manner as to prevent the rescuer from delivering chest compressions during specific physiological events such as T waves in the ECG which indicate ventricular repolarization. If a compression is delivered during a T wave, the compression may be substantially more likely to induce life-threatening ventricular fibrillation, a process known as commotio cordis. In other and more robust implementations, medical knowledge such as that just mentioned is combined with a mathematical description of the circulatory system, such as that described in Crit Care Med 2000 Vol. 28, No. 11 (Suppl.). As the author describes, the system of differential equations has been described in a number of publications. In this specific instance, "the human circulation is represented by seven compliant chambers, connected by resistances through which blood may flow. The compliances correspond to the thoracic aorta, abdominal aorta, superior vena cava and right heart, abdominal and lower extremity veins, carotid arteries, and jugular veins. In addition, the chest compartment contains a pump representing the pulmonary vascular and left heart compliances. This pump may be configured to function either as a heart-like cardiac pump, in which applied pressure squeezes blood from the heart itself through the aortic valve, or as a global thoracic pressure pump, in which applied pressure squeezes blood from the pulmonary vascular bed, through the left heart, and into the periphery. Values for physiologic variables describing a textbook normal "70-kg man" are used to specify compliances and resistances in the model. The distribution of vascular conductances (1/resistances) into cranial, thoracic, and caudal components reflects textbook distributions of cardiac output to various body regions."

Figure 9:
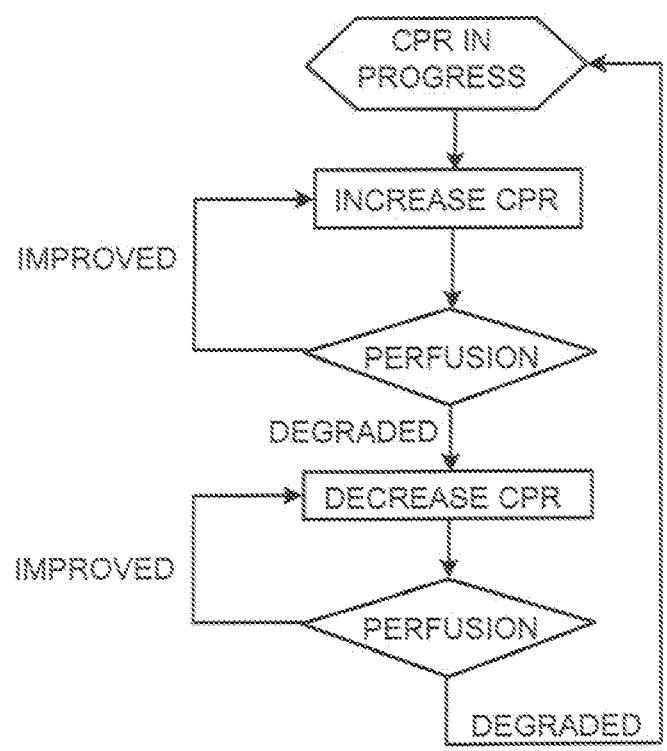
FIG. 9 is a flow chart showing a method of parameter-based CPR control feedback.

Referring to FIG. 4, a closed loop feedback method may be employed, using state space methods with the system estimation block 55 provided by a physiological model as the author describes above. The Feedback Controller 53 may employ such traditional control system methods a proportional, difference, integral (PID), or state feedback control methods, e.g., as known to those skilled in the art. As an alternative to the closed-loop control, the device may "search" for the best compression parameters by monitoring sensors as illustrated in the flowchart of FIG. 9. Although the flowchart shows only a single parameter, multiple parameters may be varied while a sensor(s) monitor the patient. The method varies parameters one at a time or in parallel and attempts to improve perfusion. The system may find that a value of a certain parameter (e.g., duty cycle) is producing improved perfusion, and continue therapy at that value, or continue to vary the parameter in a range near that value in case conditions change. Optimized search methods such as gradient steepest descent, self-annealing or genetic algorithms may also be employed.

A steepest descent algorithm works by increasing a particular parameter (e.g., rate) and seeing if it results in some measured improvement in performance of the system (e.g., EtCO2 values). If so then that particular parameter is further adjusted until the desired performance of the system is achieved. In a two-parameter system (e.g. rate and depth), it is viewed topographically, with the x-y coordinates being values of the two parameters and the z-axis representing the system performance (EtCO2). Typically, the algorithms work to minimize some output value (hence steepest descent). In some implementations, the objective would be trying to maximize the EtCO2 value. The method is typically entirely empirical, based on changing the parameter values and then measuring the system output. At any point in time, the rescuer's rate and depth are located at a particular point on the topographic map. Adjusting each parameter separately will provide a gradient (local) slope. Then, assuming a monotonic slope over a sufficient region to encompass the desired EtCO2 value, the two parameters are both adjusted to achieve the desired EtCO2 value.

Synchronizing chest compressions with underlying physiological activity may also supplement slow or bradycardic rhythms by timing compressions to occur during ventricular diastole. E.g., a patient with a rhythm of 30 beats per minute may receive better perfusion with chest compressions delivered between beats, making the effective heart rate more like 60 beats per minute. Feedback is required for the rescuer to time the compressions with some volume of blood in the ventricles and to avoid compressing on T waves.

Figure 10:
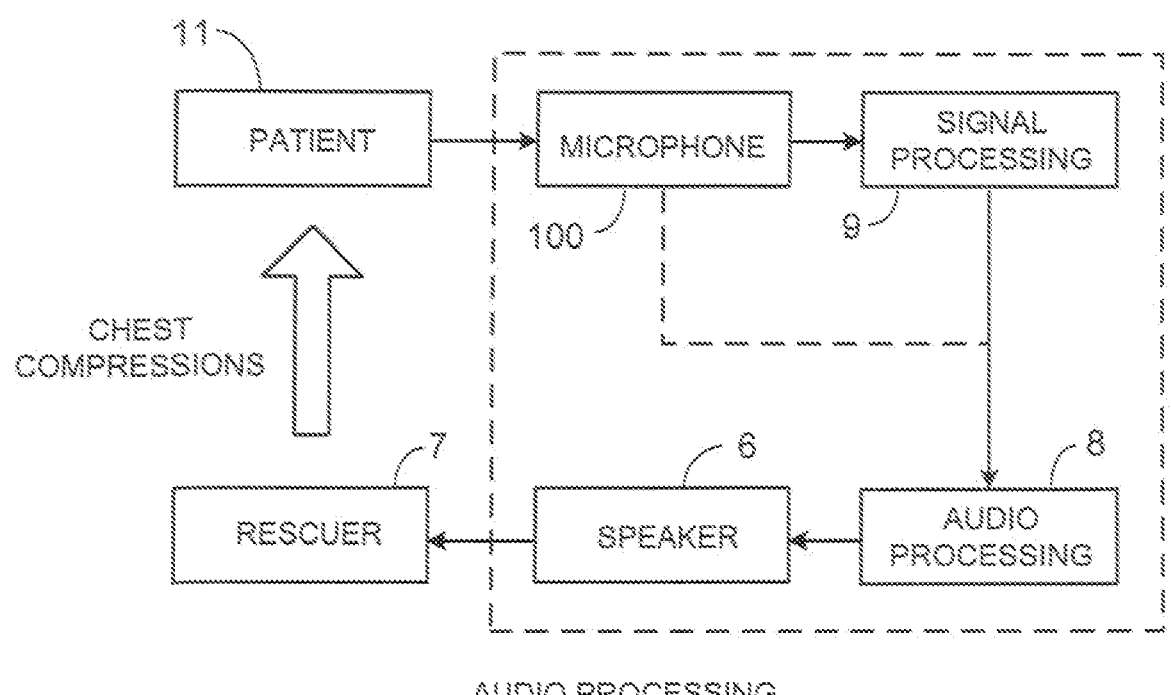
FIG. 10 is a block diagram of a resuscitation device, showing processing used to deliver audio prompts to a rescuer performing chest compressions.

Referring to FIG. 10, in other implementations, a microphone 100 or other transducer may be used to detect heart sounds. These sounds may be amplified through the speaker 6 for a trained rescuer 7 or processed to provide cues for a rescuer 7 with less training. Heart sounds may be used independently of other measures to determine CPR rates, depth, and/or duty cycle as well as to assess the effectiveness of CPR. This may be effective for a patient 11 in asystole where ECG 1, blood pressures, or pulse do not suggest a natural rate or time for the heart to be compressed. The velocity of the DPT 39 phase of the compression may be adjusted to minimize valvular regurgitation. Adequate depth of compression may be assessed by a heart sound indicating valve closure.

In other implementations, compression timing and rate may be adjusted based on any heart sound, although $S_1$ may be ideal since it indicates the start of ventricular systole. Over ventilation is estimated by the analysis of $S_2$ since splitting of the aortic and pulmonary valve closures increases with reduced intrathoracic pressure. Murmurs and other sounds may provide diagnostic information about damage to the heart and CPR parameters may be adjusted based on this information.

Other means such as ultrasound or transthoracic impedance can be used to detect and measure cardiac volume changes or blood flow. In some implementations, a catheter is inserted into the patient's esophagus with an ultrasonic probe at the distal end prior to intubation of the patient's airway. The ultrasonic probe faces posteriorly towards the cervical vertebrae and is positioned at approximately the cervical vertebra C3-C6, with the sound energy reflected off the vertebrae and providing the sensor in the probe with a robust signal for measuring blow flow in the vertebral artery by ultrasonic doppler flow measurement methods commonly in use. The benefits of such a system are several: (1) the transducer is positioned outside of the field where chest compressions are occurring, thus minimizing the motion artifact induced; (2) the method provides an excellent method of measuring blood flow to the brain; and (3) brain perfusion pressure (BPP) sufficient to induce effective flows to the brain are harder to achieve with CPR chest compressions than the coronary perfusion pressure (CPP) necessary to induce effective perfusion of the heart, thus the vertebral flow measurement is a sensitive indicator of both effective BPP and CPP during resuscitation efforts.

The vertebral arteries travel along the spinal column and cannot be felt from the outside. They join to form a single basilar artery near the brain stem at the base of the skull. The arteries supply blood to the parietal and occipital lobes of the cerebrum, part of the cerebellum, and the brain stem. The parietal lobes contain the primary sensory cortex, which controls sensation (touch and pressure), and a large association area that controls fine sensation (judgment of texture, weight, size, and shape). Damage to the right parietal lobe can cause visuo-spacial deficits, making it hard for the patient to find his/her way around new or even familiar places. Damage to the left parietal lobe may disrupt a patient's ability to understand spoken and/or written language. The occipital lobe processes visual information. It is mainly responsible for visual reception and contains association areas that help in the visual recognition of shapes and colors. Damage to this lobe can cause visual deficits. The cerebellum is the second largest area of the brain. It controls reflexes, balance and certain aspects of movement and coordination. The brain stem is responsible for a variety of automatic functions that are critical to life, such as breathing, digestion and heart beat—as well as alertness and arousal (the state of being awake). Thus, other implementations may monitor blood flow in the vertebral artery during resuscitation and adjust therapeutic interventions to maximize that flow.

Figure 13A:
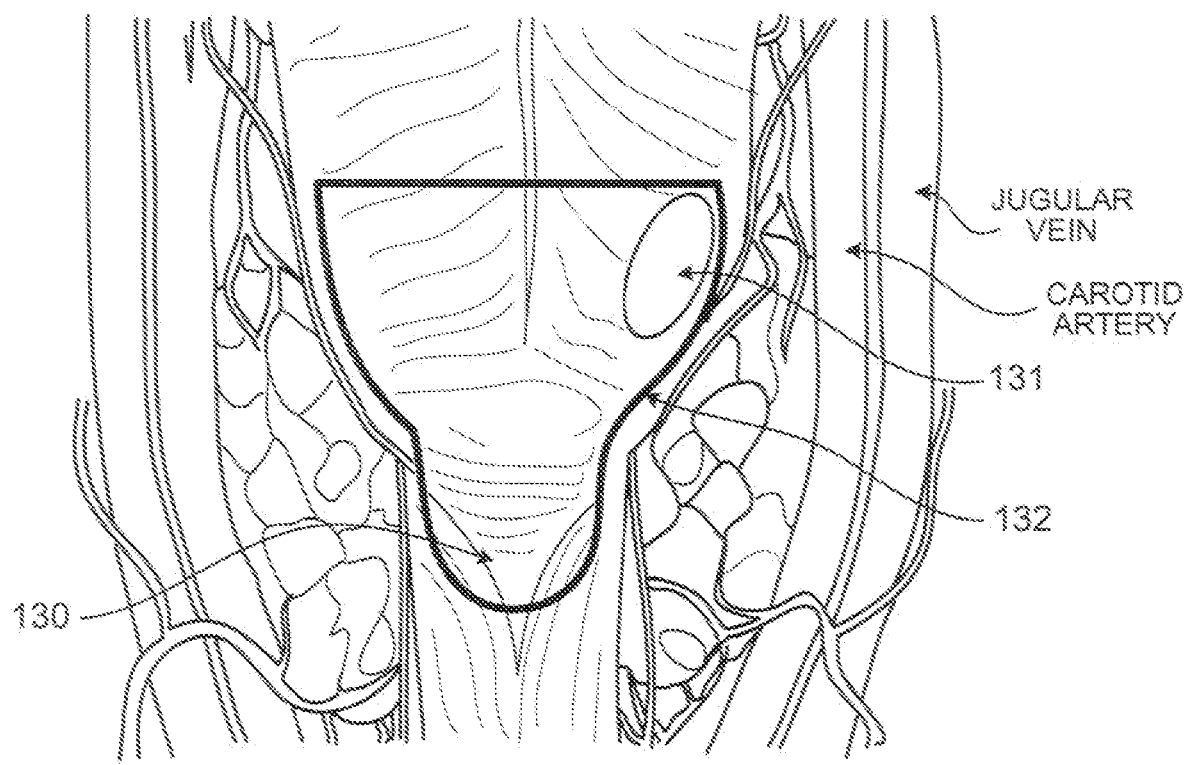
FIGS. 13A, 13B, and 13C are diagrammatic views of an ultrasonic blood flow sensor positioned in the superior end of the esophagus for providing physiological feedback.
Figure 13B:
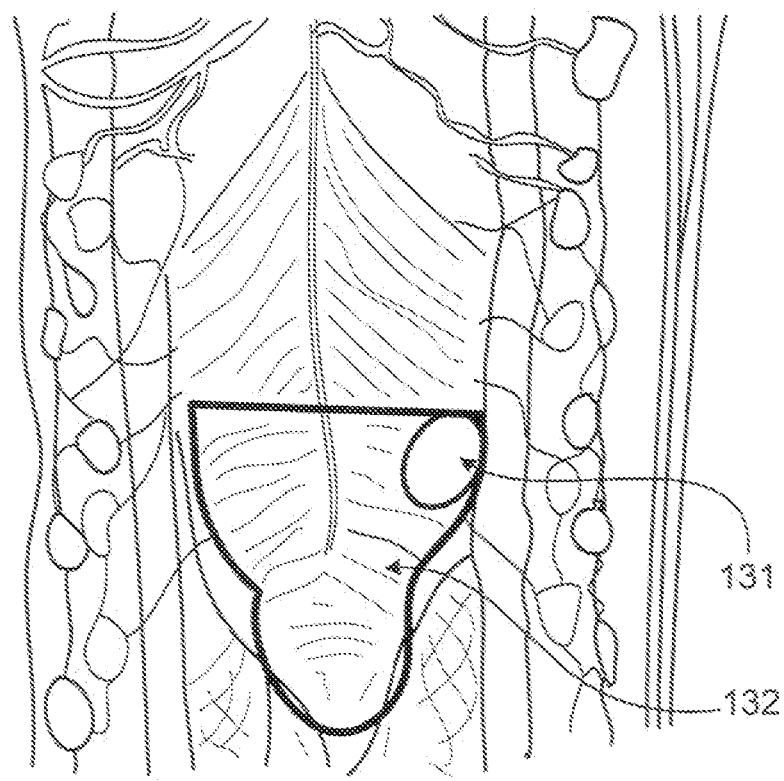
Figure 13C:
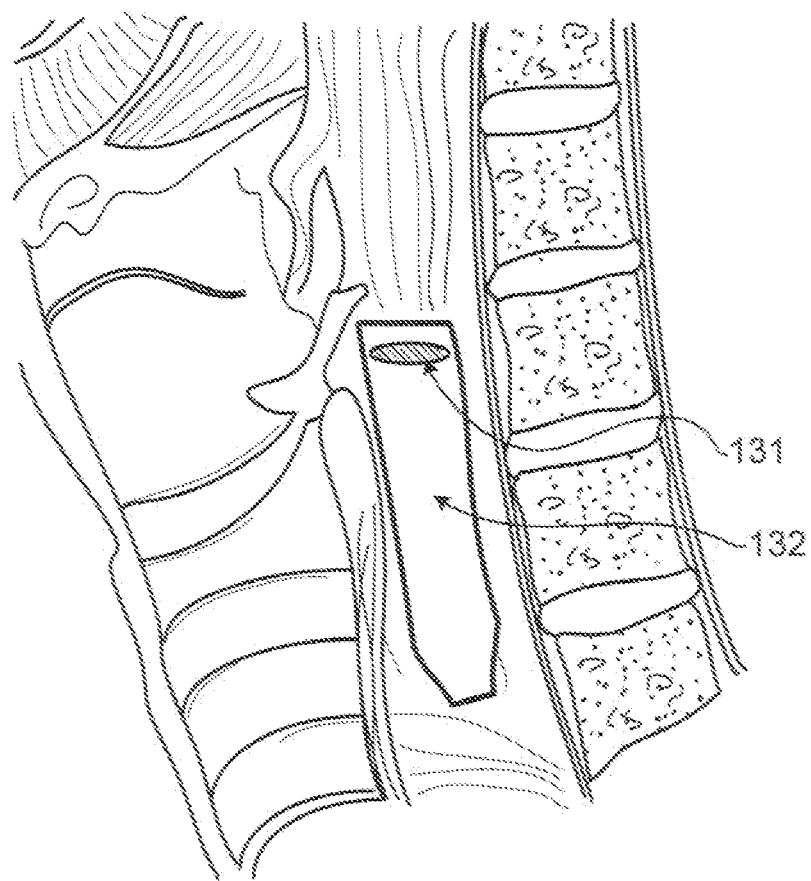

Referring to FIGS. 13A-13C, in another implementation, the ultrasonic flow sensor may be a conically shaped probe 132 positioned in the victim's lower pharynx with the narrow end of the probe seated into the superior end of the esophagus in the area of the circular esophageal muscle 130 and the wide end of the probe just above that in the lower pharynx. The ultrasonic transducer 131 is located laterally with the beam directed upward at an angle of approximately 45 degrees from the axis of the spine. The acoustic beam has been shaped, either by the use of an transducer array or by incorporation of an acoustic lens into the face of the probe, to produce a narrow elevation beam with approximately 45 degrees of azimuthal beam angle. The transducer is located in the probe to cause the acoustic beam to intersect the common carotid artery and internal jugular vein, and because of the narrow elevation beam angle, will only intersect the carotid and jugular in narrow regions to improve blood flow velocity accuracy. Blood flow velocity for both the carotid and jugular are calculated simultaneously with the Doppler shift, $2f_c v/c$, where $f_c$, v and c are the center frequency of the acoustic beam, blood velocity, and the speed of sound, respectively.

With the blood velocity profiles of both the carotid artery and jugular vein calculated, the pulsatility index is calculated as the difference of the peak aortic velocity and minimum diastolic velocity divided by the average velocity over one cycle. The Pourcelot, or resistance, index is calculated as the difference of the peak aortic velocity and minimum diastolic velocity divided by the peak aortic velocity.

An acoustically reflective material such as aluminum foil 133 laminated onto a hydrogel may be applied to the patient's neck along the acoustic beam axis to improve the signal detection capability of the transducer system.

In some implementations, a device tracks the history of CPR times and quality of CPR. This information is used as part of the advisory algorithm when the expert system recommends therapy. ECG alone has been used to classify cardiac rhythms as shockable or non-shockable. However, the success of defibrillation of cardiac pacing may be impacted by the history of CPR since ischemic tissue is less likely to depolarize in an organized way.

Figure 11:
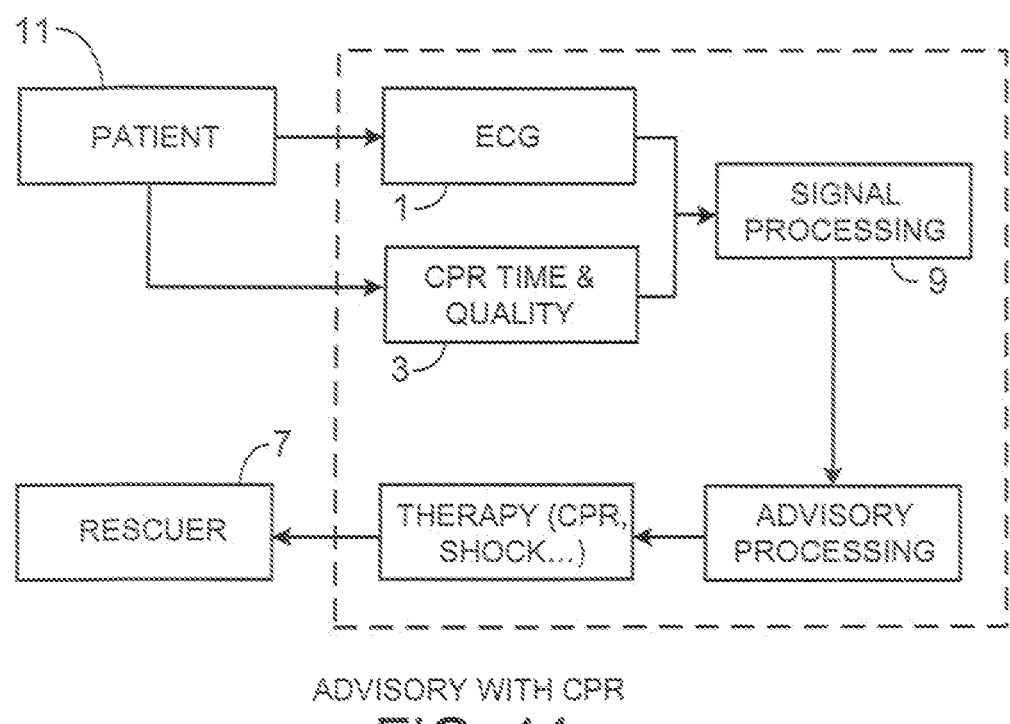
FIG. 11 is a block diagram of a resuscitation device, showing processing to provide advisory analysis with CPR feedback.

Referring to FIGS. 1 and 11, a rescuer uses an AED 10 to automatically monitor a victim during cardiac resuscitation. The AED 10 includes a speaker 6, a display 7, a signal processing module 9 including signal conditioning such as analog filters and an analog to digital converter, a processor 14, and an energy output means 13 such as a defibrillation pulse generator or other pacemaker electrical current or magnetic pulse generator. The signal processing module 9 is connected by the ECG signal acquisition module 1 to a set of ECG leads attached to the victim 11. The processor 14 monitors the victim's heart for dangerous rhythms using the ECG signals while the victim is resuscitated using chest compressions techniques. If the AED 10 detects a dangerous heart rhythm, the AED 10 generates an alarm signal. The alarm signal is noticeable to the rescuer. The AED 10 can generate a defibrillating shock to the victim when the rescuer issues a command to the AED 10. The defibrillating shock is intended to remedy the dangerous rhythm of the victim's heart.

The AED 10 uses a rhythm advisory method for (a) quantifying the frequency-domain features of the ECG signals; (b) differentiating normal and abnormal ECG rhythms, such as VF; (c) detecting the onset of abnormal ECG rhythms; and (d) making decisions about the physiological states of the heart. This frequency-domain measure is reliable with or without the presence of the chest compression artifact in the ECG signals. The AED 10, after identifying the current physiological state of the heart, can make a decision about appropriate therapeutic action for the rescuer to make and communicates the action to the rescuer using the speaker 6 and/or the display 7. The display may take the form of a graphical display such as a liquid crystal display (LCD), or may simply be one or more light emitting diodes or other such visible indicators. Bar-graph indicators such as those contained in LED bar graphs may be particularly effective at conveying the cyclical, repetitive feedback described earlier, while at the same time being less expensive, brighter and more easy to read than an LCD display. Separate visible indicators, such as bar graph LEDs, may be utilized for compression and ventilation, so as to minimize confusion on the part of the rescuer.

Figure 12A:
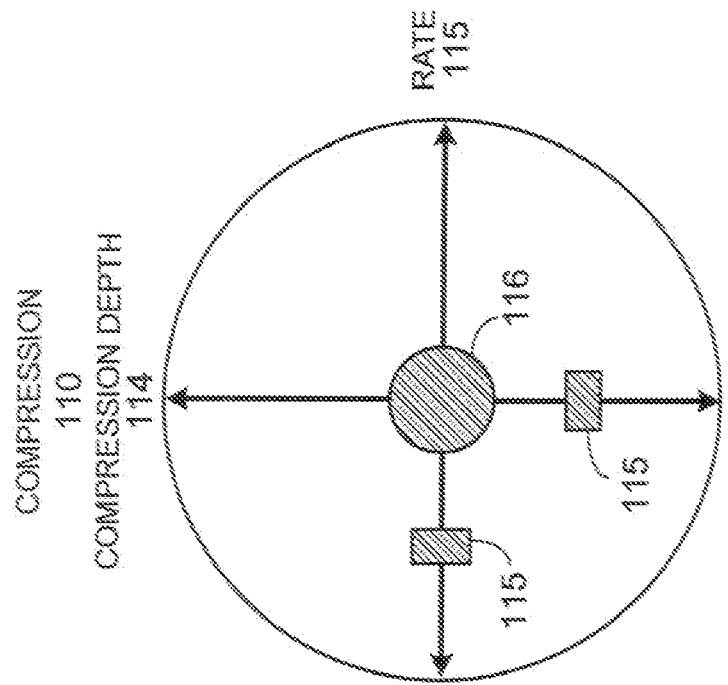
FIGS. 12A, 12B, and 12C are examples of graphical displays for providing feedback to a rescuer on ventilation and compression.
Figure 12B:
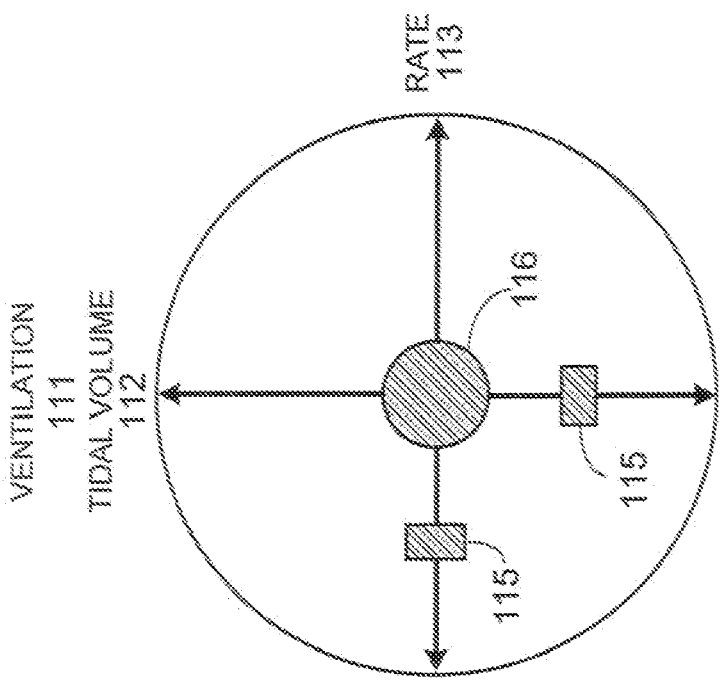

Referring to FIGS. 12A and 12B, in another implementation, the system estimation block 55 provided by a physiological model composed of an interlinked set of difference equations, e.g., as Babbs described above, is used to provide a graphical feedback such as on an LCD display. There may be situations during which rescuers are preoccupied with communication with other rescuers and may not be able to focus on their compressions on a compression-by-compression basis necessary to achieve the desired phase synchronization (entrainment). While the lack of phase synchronization (entrainment) will result in reduced efficacy, there may still be benefit to be gained by providing to the rescuer a succinct visual feedback of the four main resuscitation parameters: compression depth 114 and rate 115, and ventilation tidal volume 112 and rate 113, on a compression by compression basis. This visual feedback may take the form of separate dials 110, 111, one for compression and one for ventilation, provided on a portion of the LCD display of a resuscitation control panel. Each dial may have the two key parameters related to its performance displayed on orthogonal axes. Contrasting status bars 115 indicate the current status of performance of each of the parameters, while a green central region 116 indicates the desired target zone. Status bars 115 residing either to the right or below the central regions 116 indicate that the relevant parameter needs to be increased while status bars 115 above or to the right of the central region 116 indicate that the relevant parameter needs to be decreased. In some cases, only the ventilation rate may be shown. Alternatively, the dials may be composed of additional indicators, e.g., five indicators corresponding to: ventilation tidal volume too high and too low; ventilation rate too high and too low; compression depth too deep and too shallow; compression rate too fast and too slow; and the two central regions. If one of the two parameters for a dial is too high or low that particular indicator will light while the second parameter that is being performed properly will cause the central region 116 to change from red to yellow. When both parameters for a particular dial are being performed correctly, the central region will turn green. The indicators may be LEDs or may be regions on an LCD.

These implementations provide a simple physiological model in the feedback loop. It takes about 35-45 seconds of good chest compressions to develop good blood flow, yet it only takes 5 seconds for that blood flow to drop down after the rescuer stops CPR. The problem is that people tend to stop chest compressions too often. By using a physiological model, e.g., the Babbs model or a more simple one, each compression increases an indicator by some amount and that amount depends on depth of compression. The result is an approximation of the way that actual coronary perfusion pressure reacts for the victim.

As noted, the Babbs physiological models, which have been verified in animal models and human clinical studies, show that it actually takes approximately 30-45 seconds of good CPR to bring the coronary perfusion pressure, CPP, up to some decent value. CPP is a measure of the blood pressure going into the coronary circulation—what supplies blood to the heart muscle. While CPP is slow to rise during compressions, CPP falls off precipitously when good CPR stops, within about 10 seconds.

In another implementation, a physiological model is incorporated into the feedback loop so that what is presented visually to the rescuer is a Perfusion Performance Indicator (PPI), providing them a simple indicator of the physiological impact of their CPR on the cardiac arrest victim. In a simple implementation, perfusion is modeled as a leaky vessel which is filled with a certain volume with each compression, that volume being dependent on the depth of the compression. In between each compression, some of that volume leaks out of the vessel.

Figure 12C:
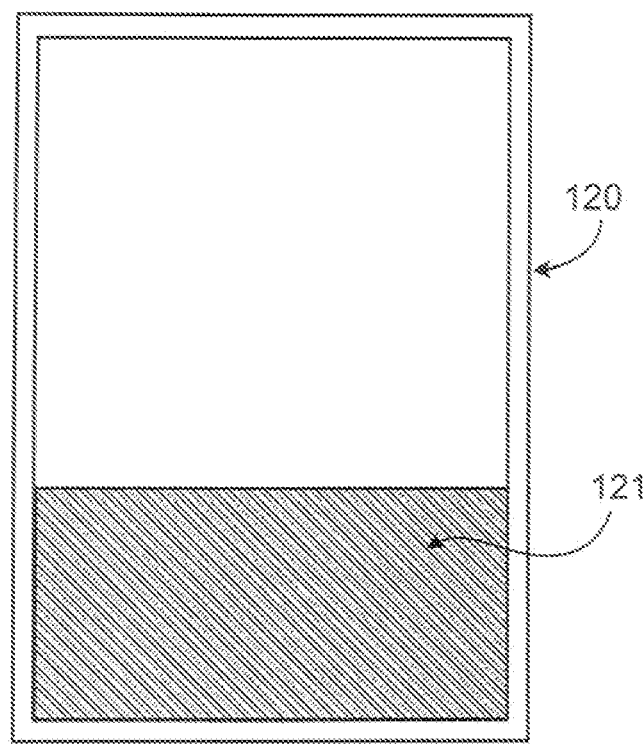

The pseudocode listed below implements one possible physiological model. It was desired to bring the Perfusion Performance Indicator to 100% in 50 good (proper depth) compressions (about 30 seconds), but at the same time fall off at a rate that brings the PPI to zero in 15 seconds. The particular values chosen were due in part to new CPR guidelines being proposed by the American Heart Association (AHA) of a 30:2 ratio for compressions to ventilations. With the pause that typically occurs when ventilations are performed, the PPI will drop significantly by the end of the pause that results from the mid-minute ventilation cycle, but if good compressions are performed will be back up to 100 immediately prior to the defibrillation shock that would occur at the end of the one-minute CPR interval. The goal of the rescuer is to get PPI as close to 100 right before the shock. PPI gets reset to zero after the shock, so the rescuer is motivated to begin compressions immediately after shock. Another possible graphical feedback implementation is shown in FIG. 12C. The outside thick band (approximately ⅛ inch wide) of PPI block 120 turns green for 1 second after a good compression (greater than 1.5 inch) is delivered, then reverts to black. The band turns red for 1 second when a "poor" compression (less than 1.5 inch) is delivered, and then reverts to black again. The goal is to keep the PPI outline band 120 green. The PPI block 121 "fills up" based on Perfusion_Perf_Ind value (full when Perfusion_Perf_Ind=32896). More complex implementations may incorporate interactions of ventilations with compressions or more complete models as described by Babbs.

One possible pseudocode implementation is as follows:

```
Perfusion_Perf_Ind is 0 - 32896 number.
CONST
DECREMENT_INTERVAL == 100 (* number of milliseconds in
    decrement interval*)
DROPOFF == 15 * 1000 / SAMPLE_INTERVAL (* 15 seconds,
    adjustable*)
COMPRESS_RATE == 100 (*compressions per minute)
NUM_OF_COMPRESS_TO_100_PERCENT == 50;
PPI_DECREMENT== 32896 / DROPOFF;
IDEAL_INCREASE_PER_COMPRESS == 32896 / 50 + (
    PPI_DECREMENT * 60 / COMPRESS_RATE)
IDEAL_COMPRESS_DEPTH == 2 (*inches*)
Function
{
For each decrement interval (for now 100 ms), decrement
    Perfusion_Perf_Ind by PPI_DECREMENT until
    Perfusion_Perf_Ind equals zero;
For each compression detected,
if compression depth is > 1 inch (*note, NOT 1.5 inches*)
{
Compression_efficacy = compression depth /
    IDEAL_COMPRESS_DEPTH;
Perfusion_Perf_Ind = Perfusion_Perf_Ind +
    IDEAL_INCREASE_PER_COMPRESS * Compression_efficacy;
If Perfusion_Perf_Ind > 32896, then Perfusion_Perf_Ind = 32896;
}}
```

The AED 10 may incorporate functionality for performing additional therapeutic actions such as chest compressions, ventilations, or delivery of intravenous solution containing metabolic or constitutive nutrients. Based on the results of the analysis of the rhythm advisory method, the AED 10 may automatically deliver the appropriate therapy to the patient 11. The AED 10 may also be configured in "advisory" mode wherein the AED 10 will prompt the caregiver after the AED 10 has made a determination of the best therapy, and acknowledgement by the caregiver/device operator, in the form of a button press or voice-detected acknowledgement, is required before therapy is delivered to the patient.

The AED 10 then analyzes the ECG signals to predict defibrillation success as well as to decide whether it is appropriate to defibrillate or to deliver an alternative therapy such as chest compressions, drugs such as epinephrine, constitutive nutrients such as glucose, or other electrical therapy such as pacing.

In some implementations, one or more therapeutic delivery devices 15 automatically deliver the appropriate therapy to the patient. The therapeutic delivery devices 15 are physically separate from the defibrillator AED 10 and control of the therapeutic delivery devices 15 may be accomplished by a communications link 16. The communications link 16 may take the form of a cable connecting the devices but preferably the link 16 is via a wireless protocol such as Bluetooth or a wireless network protocol such as Institute of Electrical and Electronics Engineers (IEEE) 802.11. The therapeutic delivery device 16 can be a portable chest compression device that is commercially available as the Autopulse™, provided by Revivant of Sunnyvale, Calif. In other examples, the therapeutic delivery device 16 is a drug infusion device that is commercially available as the Power Infuser™, provided by Infusion Dynamics of Plymouth Meeting, Pa., or the Colleague CX™, provided by Baxter Healthcare Corp., of Round Lake, Ill. The therapeutic delivery device 16 can be a ventilator that is commercially available as the iVent™, provided by Versamed of Pearl River, N.Y. The therapeutic delivery device 16 can also include multiple therapies such as defibrillation, chest compression, ventilation and drug infusion.

In other implementations, control and coordination for the overall resuscitation event and the delivery of the various therapies may be accomplished by a device 17 or processing element external to the AED 10. For instance, the device 17 may download and process the ECG data from the AED 10, analyze the ECG signals, perform the determinations based on the analysis, and control the other therapeutic devices 16, including the AED 10.

In other implementations, the AED 10 may perform all the processing of the ECG, including analyzing the ECG signals, and transmit to the control device 17 only the final determination of the appropriate therapy, whereupon the control device 17 would perform the control actions on the other linked devices 30. The control device 17 preferably is a laptop computer running automated patient record software such as Tablet PCR, manufactured by ZOLL Data Systems of Denver, Colo.

Many other implementations of the invention other than those described above are within the invention, which is defined by the following claims.

What is claimed is:

1. A system for delivering cardiac stimulation during cardiopulmonary resuscitation (CPR) chest compressions comprising a memory, a processor, and associated circuitry wherein the processor is configured to:
   receive, from a motion sensor located externally to a patient's chest, a motion sensor signal indicative of chest wall motion that is caused by a series of repetitive externally applied chest compressions;
   synchronize a delivery of at least one externally applied chest compression in the series of repetitive externally applied chest compressions to a myocardial response comprising an improvement in myocardial tone and induced by repetitive cardiac stimulation therapy pulses that cause an insufficient hemodynamic response from a metabolically compromised myocardium and are generated by an energy output device of an external defibrillator, and adjust a start time of the at least one externally applied chest compression and a start time of the repetitive cardiac stimulation therapy pulses relative to one another in response to drug induced improvements in the myocardial tone, wherein the repetitive cardiac stimulation therapy pulses precede the delivery of the at least one externally applied chest compression, and wherein the synchronized delivery is based at least in part on the motion sensor signal indicative of the chest wall motion that is caused by the series of repetitive externally applied chest compressions.

2. The system of claim 1 wherein the repetitive cardiac stimulation therapy pulses comprise electrical pulses or magnetic pulses.

3. The system of claim 1 wherein the motion sensor is an accelerometer.

4. The system of claim 1 wherein the series of repetitive externally applied chest compressions are automated chest compressions.

5. The system of claim 1 wherein the series of repetitive externally applied chest compressions are manual chest compressions.

6. The system of claim 5 wherein the processor is configured to:

determine, based at least in part on the motion sensor signal, a latency between a feedback instruction to a rescuer to deliver the at least one externally applied chest compression and the delivery of the at least one externally applied chest compression by the rescuer; and based on the determined latency, adjust a timing of the feedback instruction to the rescuer to deliver the at least one externally applied chest compression to adjust the start time of the at least one externally applied chest compression and the start time of the repetitive cardiac stimulation therapy pulses relative to one another.

7. The system of claim 6 wherein the processor is configured to determine the latency based, at least in part, on a tracking filter applied to the motion sensor signal.

8. The system of claim 1 wherein the energy output device comprises at least one of an electrical current generator and a magnetic pulse generator.

9. The system of claim 1, wherein the external defibrillator is configured to provide a perfusion performance indicator indicative of blood flow from the series of repetitive externally applied chest compressions, wherein the blood flow is based at least in part on the improvement in the myocardial tone.

* * * * *